(12) United States Patent
Masuda et al.

(10) Patent No.: US 7,132,098 B2
(45) Date of Patent: Nov. 7, 2006

(54) METHOD FOR THE TREATMENT OF CHEMONUCLEOLYSIS

(76) Inventors: Koichi Masuda, 827 Lavergne, Wilmette, IL (US) 60091; Eugene J-M. A. Thonar, 14503 S. Pheasant, Lockport, IL (US) 60441; Howard An, 486 Somerset Hills Ct., Riverwood, IL (US) 60015

( * ) Notice: Subject to any disclaimer, the term of this patent is extended or adjusted under 35 U.S.C. 154(b) by 107 days.

(21) Appl. No.: 10/373,669

(22) Filed: Feb. 24, 2003

(65) Prior Publication Data
US 2004/0033221 A1 Feb. 19, 2004

Related U.S. Application Data

(63) Continuation of application No. 09/366,021, filed on Aug. 2, 1999, now abandoned.

(60) Provisional application No. 60/103,161, filed on Oct. 6, 1998.

(51) Int. Cl.
*A61K 38/47* (2006.01)
(52) U.S. Cl. ................................. 424/94.61
(58) Field of Classification Search ............... 424/94.6, 424/1.41, 94.61
See application file for complete search history.

(56) References Cited

U.S. PATENT DOCUMENTS

| 4,696,816 A | 9/1987 | Brown |
| 5,723,331 A | 3/1998 | Tubo et al. |
| 6,063,378 A | 5/2000 | Nohara et al. |
| 6,080,579 A | 6/2000 | Hanley, Jr. et al. |

FOREIGN PATENT DOCUMENTS

| EP | 000569541 B1 * | 3/1995 |
| WO | WO 92/13565 | 8/1992 |

OTHER PUBLICATIONS

Kato, F, et al., Rinsho Seikeigeka (1987); 22 (8): 965-974. Chemonucleolysis and response of postchemonucleolytic intervertebral disc to bone morphogenetic protein BMP.
Gruber et al., J Bone Mineral Res (1996) 11 (Suppl. 1): s300. Transforming growth factor-beta 1 regulates proliferation and proteoglycan gene expression in diseased human intervertebral disc cells.
Dieudonne, et al. J of Bone and Mineral Research, 9(6), 771-780. Opposite effects of osteogenic protein and transforming growth factor-beta on chondrogenesis in cultured long bone rudiments.
Supplementary Partial European Search Report issued Oct. 20, 2004 for European Patent Application No. 99938920.8.
Kato, "Experimental Study of Chemical Spinal Fusion in the Rabbit by Means of Bone Morphogenetic Protein," Journal of the Japanese Orthopaedic Association, vol. 64, No. 5, 1990, pp. 442-452.
Flechtenmacher, et al., "Recombinant Human Osteogenic Protein 1 is a Potent Stimulator of the Synthesis of Cartilage Proteoglycans and Collagens by Human Articular Chondrocytes," Arthritis and Rheumatism, vol. 39, No. 11, Nov. 1996, pp. 1896-1904.
Sugimura, et al., "Experimental Chemonucleolysis with Chondroitinase ABC in Monkeys," Spine, vol. 21, No. 2, 1996, pp. 161-165.

* cited by examiner

*Primary Examiner*—Michele Flood
(74) *Attorney, Agent, or Firm*—Foley & Lardner LLP

(57) ABSTRACT

The invention relates to a method of treatment for a mammal in need of chemonucleolysis. The method comprising the administration of an effective proteoglycan cleaving amount of a proteoglycan-degrading enzyme and an effective amount of a growth factor effective in promoting the synthesis of a matrix component. The proteoglycan-degrading enzyme is preferably chondroitinase. The growth factor is preferably osteogenic protein. The proteoglycan-degrading enzyme and the growth factor are preferably administered simultaneously.

20 Claims, 12 Drawing Sheets

Effects of rhOP-1 on PG and Collagen Synthesis

METHOD FOR THE TREATMENT OF CHEMONUCLEOLYSIS

CROSS REFERENCE TO RELATED APPLICATIONS

This application claims the benefit of U.S. Ser. No. 60/103,161, filed Oct. 6, 1998, which is incorporated herein in its entirety by reference.

GOVERNMENT SUPPORT

This invention was made with U.S. governmental support under NIH grants 2-P50-AR39239 and AG04736. The U.S. government has certain rights in the invention.

FIELD OF THE INVENTION

The invention relates to a method of treatment for a mammal in need of chemonucleolysis. More specifically, the invention relates to a method of treatment comprising the administration of an effective proteoglycan cleaving amount of a proteoglycan-degrading enzyme and an effective proteoglycan synthesizing amount of a growth factor.

BACKGROUND OF THE INVENTION

Low back pain constitutes a devastating economic burden for individuals and society. In industry, it is the most frequent cause of disability: the number of working days lost per year in the United States is in excess of 100 million. Kramer, J., *Intervertebral Disk Disease*. Stuttgart, George Thieme Verlag (1981). Over 500,000 workers are affected in the U.S. each year, costing over 20 billion dollars. Kranzler, L. I., L. et al., *Neurologic Clinics* 3: 2 (1985). Low back pain is almost always associated with pathological changes in one or more intervertebral disks of the lumbar spine.

Intervertebral disks are a specialized fibrocartilaginous connective tissue whose function is to resist the compressive, rotational and tensile stresses applied to the vertebral column. Humzah, M. D. et al., *Anat. Rec.* 220(4): 337–56 (1988). These disks act as a hydrostatic shock absorber that cushions the forces generated between two vertebrae and help these vertebrae articulate smoothly with one another. The disk is a complex structure consisting of two interdependent, but morphologically distinct regions: the nucleus pulposus (NP), an inner gelatinous cushion rich in proteoglycans (PGs), and an outer annulus fibrosus (AF) made up of concentric lamellae rich in collagen fibers.

The metabolism of the cells that produce and maintain the extracellular matrix of both the NP and AF is poorly understood. The matrix in the NP is very similar to that found in articular cartilage. Jahnke, M. R. et al., *Biochemical Journal* 251(2): 347–56 (1988). It is synthesized and maintained throughout adult life by relatively few cells. More than 75% of NP cells are chondrocyte-like, but a significant number of large notochordal cells are present, especially prior to adult life. Maldonado, B. A. et al., *Journal of Orthopaedic Research* 10(5): 677–90 (1992). It is not clear if both NP cell types synthesize the large-molecular-weight hydrophilic PG, termed aggrecan, that constitutes the most abundant molecule in the tissue. As in articular cartilage, these aggrecan molecules interact extracellularly with long linear stands of hyaluronan (HA), forming aggregates that become entangled in a fibrillar network made up principally of type II collagen. Thonar, E. J. et al., *Rheum. Dis. Clin. North Am.* 19(3): 635–57 (1993). The swelling, fluid- and ion-transport properties, and the intrinsic mechanical properties of the collagen-aggrecan solid matrix govern the deformational behavior of the NP. The collagen network gives the tissue tensile strength and hinders expansion of the viscoelastic, under-hydrated, aggrecan molecules that provide compressive stiffness and enable the tissue to undergo reversible deformation.

The AF contains a relatively homogeneous population of chondrocyte-like cells (Maldonado, B. A. et al., *Journal of Orthopaedic Research* 10(5): 677–90 (1992)) that synthesize a matrix richer in collagen and poorer in PGs than cells from the NP. Importantly, some of the cells synthesize PG and collagen molecules not normally found in significant amounts in cartilage. Wu, J. J. et al., *Biochemical Journal* 248(2): 373–81 (1987); Mayne, R. and Brewton, R. G., "Extracellular matrix of cartilage collagen," in *Joint Cartilage Degradation. Basic and Clinical Aspects* (Woessner, J. R. and Howell, D. S., eds.), Marcel Dekker, Inc., New York, pp. 81–108 (1993); Thonar, E. J.-M. A. et al., "Body fluid markers of cartilage changes in osteoarthritis," in *Rheumatic Disease Clinics of North America: Osteoarthritis* (Moskowitz, R., ed.), W. B. Saunders Co., Philadelphia, pp. 634–658 (1993). The AF is thus usually classified as a fibrocartilage: it is built for strength rather than to provide reversible deformation.

The metabolism of intervertebral disk cells is much less well known than that of chondrocytes from articular cartilage. Progress in this area has been limited by the costly nature of in vivo experimental approaches and the restrictions imposed in the past by the lack of an appropriate culture system to study the metabolism of the cells. Chiba et al. (Chiba, K. et al., "Nucleus pulposus and annulus fibrosus cells cultured in alginate: characterization of matrix metabolism in different compartments," *Transactions of 2$^{nd}$ Combined Meeting of the Orthopaedic Research Societies of U.S.A., Japan, Canada and Europe*, p. 32 (1995)) have developed a cell culture system that takes advantage of an alginate bead culture system that was developed and refined to study the metabolism of phenotypically-stable chondrocytes and the turnover of the matrix they form de novo. Häuselmann, H. J., et al., *Matrix* 12(2): 116–29 (1992); Häuselmann, H. J. et al., *J. Cell Sci.* 107: 17–27 (1994); Mok, S. S. et al., *J. Biol. Chem.* 269(52): 33021–7(1994); Petit, B., et al., *Experimental Cell Research* 225: 151–161 (1996). As in articular chondrocytes, intervertebral disk cells entrapped in these alginate beads also reform an extracellular matrix. Chiba, K., et al. *Spine* 22(24): 2885–93 (1997). This cell culture system can be used to study the effect of compounds on the metabolism of both AF and NP cells. This cell culture system can distinguish between changes occurring in the metabolically active (cell-associated) and-inactive (further removed) compartments of the matrix. Chiba et al. have also shown that it is feasible to entrap a whole rabbit intervertebral disk in alginate gel. Chiba, K., G. B. J. Andersson, et al., *Ortho. Res. Soc. Trans.* 21:190 (1996). This approach, which more closely mimics the in vivo situation, leads to improved retention of the disk structure and promotes high metabolic activities.

Lumbar intervertebral disk herniation is one of the most common causes of lower back pain. Disk herniation is initially conservatively treated with physical therapy, but other more invasive treatment modalities are sometimes required. For example, chemonucleolysis, the dissolution of intervertebral disk tissue using a locally injected enzyme, has been used for over thirty years. Olmarker, et al. *Clin. Orthopaedics and Related Res.* 257:274 (1990). As PGs contribute most of the swelling pressure in the NP, intradiscal injections of enzymes that degrade PGs (Bradford, D. S., et al., *Journal of Bone and Joint Surgery—American Volume* 65(9): 1220–31 (1983); Hill, G. M. et al., *Clinical Orthopaedics and Related Researches* 225: 229–233 (1987)) or collagens cause a decompression of the nerve root entrapped by the herniated mass, and thus help relieve pain. There is preliminary histological evidence that the cells in disks treated with these enzymes can replenish the NP with PGs, (Bradford, D. S., et al., *Journal of Bone and Joint Surgery-American Volume* 65(9): 1220–31 (1983)) helping to reestablish the shock-absorbing properties of the intervertebral cushion and, most importantly, to normalize forces and stresses placed upon adjacent disks.

Complications can arise from chemonucleolysis when it is performed with two commonly used enzymes, namely chymopapain and collagenase. Kitchel and Brown report that chymopapain treatment can lead to subarachnoid hemorrhage, paraplegia, anaphylaxis, and even death. *Clin. Orthopaedics and Related Res.* 284:63 (1992). Olmarker et al. note that the injected chymopapain is both neurotoxic and allergenic, and that treatment with collagenase may lead to neurologic deficits. *Clin. Orthopaedics and Related Res.* 257:274 (1990).

Because the painful sciatica associated with disk herniation is often not relieved by conservative treatments, including physical therapy and chemonucleolysis, many patients undergo disk surgery. Hill, G. M. et al., *Clinical Orthopaedics and Related Researches* 225: 229–233 (1987). However, surgical results are not always satisfying and importantly, this approach is far from optimal as removal of a lumbar intervertebral disk causes significant destabilization of the lower spine and predisposes adjacent intervertebral disks to degeneration in later years. Hill, G. M. et al., *Clinical Orthopaedics and Related Researches* 225: 229–233 (1987).

Recently, newer treatment modalities for chemonucleolysis have been developed that avoid some of the problems inherent in the use of proteases such as chymopapain and collagenases, and may avoid the need for surgical intervention. One such chemonucleolytic enzyme is chondroitinase ABC, a product of *Proteus vulgaris*. Chondroitinase ABC is an endo-N-acetyl-D-hexosaminidase that degrades mucopolysaccharides such as chondroitin sulfate, dermatan sulfate, chondroitin and hyaluronic acid. Takahashi et al., *Spine* 21:2405 (1996). Olmarker et al. note that chondroitinase ABC is much less injurious to spinal tissue than chymopapain. *Spine* 21:1952 (1996).

Osteogenic protein-1 (OP-1), also known as Bone Morphogenetic Protein-7 (BMP-7), is a member of the TGF-β superfamily that exerts potent effects on osteocyte and chondrocyte differentiation and metabolism. Asahina, I., et al., *J. Cell Biol.* 123(4): 921–33 (1993). The bone morphogenetic proteins were shown to induce new bone formation when injected subcutaneously in the rat. Cook, S. D. et al., *Clin. Orthop.* 324: 29–38 (1996). Recombinant human OP-1 (rhOP-1) has been shown to promote growth and differentiation of osteoblasts in vitro. Sampath, T. K., et al., *J. Biol. Chem.* 267: 20352–20360 (1992). It also causes differentiation of mesenchymal stem cells along chondrogenic and osteogenic pathways. Asahina, I., *J. Cell. Biol.* 123(4): 921–33 (1993). Recombinant human OP-1 also exerts specific effects on chondrocytes. Chen, et al. demonstrated that OP-1 promotes growth of chick sternal chondrocytes. Chen, P. et al., *J. Cell. Sci.* 108(Pt 1): 105–14 (1995). In this system, induction of synthesis of type X collagen was noted, suggesting that OP-1 exerted an effect on chondrocyte maturation as well. Bovine chondrocytes, in contrast, did not express type X collagen in response to OP-1 but did exhibit increased synthesis of PGs and type II collagen. Chen, P. et al., *Biochem. Biophys. Res. Commun.* 197(3): 1253–9 (1993). Growth factors are not used in existing chemonucleolysis treatment utilizing protease enzymes such as chymopapain and collagenase because these enzymes cleave or degrade the growth factors.

There is thus a need for a chemonucleolysis treatment that not only provides relief from the symptoms of intervertebral disk herniation, but also provides enhanced stability and repair of the AF and NP. Similarly, there is a need for a chemonucleolysis treatment that provides sufficient mechanical support to the spinal column, and that obviates the need for invasive surgical intervention. There is further a need to have a method of chemonucleolytic treatment that requires only one treatment modality for both dissolution of the intervertebral disk tissue while providing both stability and repair of that tissue. The treatment method of the present invention provides such a method.

BRIEF SUMMARY OF THE INVENTION

A method of this invention involves a treatment comprising administering to a mammal in need of chemonucleolysis an effective proteoglycan cleaving amount of a proteoglycan-degrading enzyme; and an amount of a growth factor effective for stimulating the formation of a matrix component. In a preferred embodiment, the matrix component is proteoglycan. In another preferred embodiment, the matrix component is collagen.

In another aspect, the invention contemplates a method of repairing the matrices of nucleus pulposus and/or annulus fibrosus cells after chemonucleolysis by a proteoglycan-degrading enzyme comprising administering to a mammal in need of such treatment an effective proteoglycan synthesizing amount of a growth factor.

In yet another aspect, the invention contemplates a method of replenishment of nucleus pulposus and/or annulus fibrosus cells after chemonucleolysis by a proteoglycan-degrading enzyme comprising administering to a mammal in need of such treatment an effective proteoglycan synthesizing amount of a growth factor.

A preferred proteoglycan-degrading enzyme is chondroitinase. Preferred chondroitinases include chondroitinase AC, chondroitinase B, and chondroitinase C. A particularly preferred chondroitinase is chondroitinase ABC.

A preferred growth factor is osteogenic protein. A particularly preferred osteogenic protein is OP-1. Another preferred growth factor is transforming growth factor β.

In a preferred embodiment, the proteoglycan-degrading enzyme and the growth factor are administered simultaneously.

In another aspect, the present invention contemplates a composition of matter comprising a proteoglycan-degrading enzyme and a growth factor. Preferably, the proteoglycan-degrading enzyme and the growth factor are formulated as a pharmaceutical composition containing a pharmaceutically acceptable carrier and/or vehicle.

In a still further aspect, the present invention contemplates a kit comprising a proteoglycan-degrading enzyme and a growth factor. In a preferred embodiment, the kit comprises a vessel containing a proteoglycan-degrading enzyme and a vessel containing a growth factor. In another preferred embodiment, the kit comprises a vessel containing a proteoglycan-degrading enzyme and a growth factor. Any of these kits optionally include instructions for using the proteoglycan-degrading enzyme and the growth factor in chemonucleolysis.

The present invention offers general benefits and advantages. One advantage is that the deleterious effects of chemonucleolysis on the structure of intervertebral disk matrices can be counteracted by including as part of the treatment a growth factor effective in promoting repair of the disk structures. A benefit of the present invention is that the administration of a growth factor is not impaired by the administration of proteolytic chemonucleolysis enzymes. Another advantage is that the administration of a chemonucleolytic enzyme can occur concurrently with the administration of a growth factor protein since the enzyme has no proteolytic activity and thus does not inactivate the growth factor. A further benefit is that this method of treatment provides fewer complications than known chemonucleolysis treatments.

Still further benefits and advantages of the present invention will be apparent to a person of ordinary skill from the description that follows.

BRIEF DESCRIPTION OF THE DRAWINGS

In the drawings forming a portion of this disclosure.

DETAILED DESCRIPTION OF THE INVENTION

Figure 1:
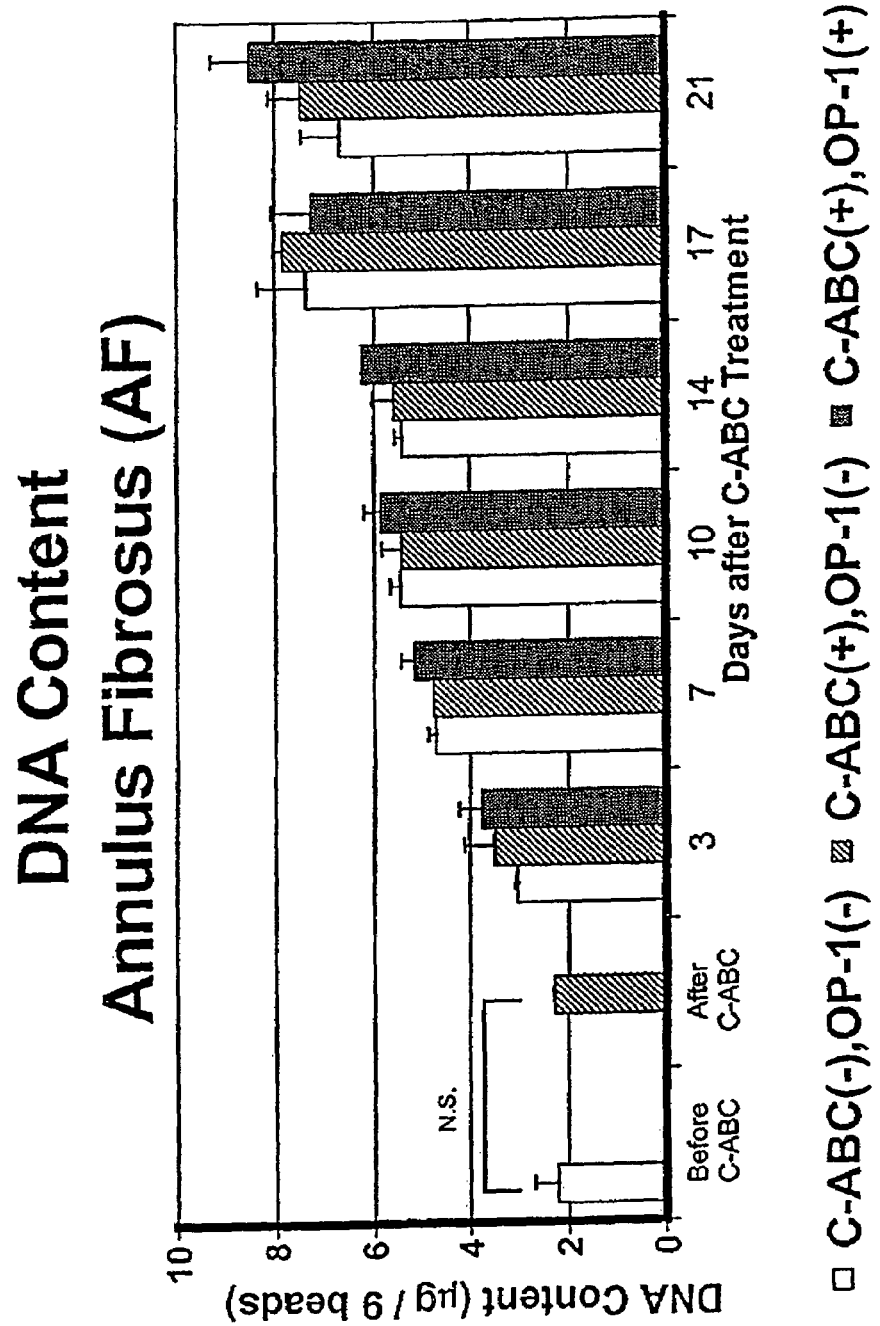
FIG. 1 illustrates the effects of OP-1 on the DNA content, in micrograms per 9 alginate beads, of the annulus fibrosus ("AF") treated with chondroitinase ABC ("C-ABC"). The open bars represent data for cells not treated with C-ABC or OP-1 ("C-ABC(−), OP-1(−)"). The hatched bars represent data for cells treated with C-ABC only ("C-ABC(+), OP-1(−)"). The filled bars represent data for cells treated with both C-ABC and OP-1 ("C-ABC(+), OP-1(+)"). The data are all presented with standard error bars. "N.S." indicates that the difference in DNA content in the AF before and after C-ABC treatment at time zero is not significant.

A method of the invention contemplates treatment of a mammal in need of chemonucleolysis. A mammal in need of such treatment is identified by, for example, differential diagnosis following presentation with lower back pain. Intervertebral disk herniation can be diagnosed by, for example, complaints of a history of lower back pain, followed by physical examination of the lower back. Diagnostic radiographic imaging, such as MRI, can be performed to confirm the diagnosis. Chemonucleolysis is usually indicated in mammals that are refractory to physical therapy where there is bulging of the disk herniation.

Chemonucleolysis is typically performed by direct injection into the intervertebral space of an enzyme that causes the dissolution of intervertebral disk tissue by protein hydrolysis. When non-proteolytic proteoglycan-degrading enzymes are used to disrupt the intervertebral disk tissue, the glycosaminoglycan chains of proteoglycans present in the AF and NP are enzymatically cleaved while the core protein of the proteoglycan remains intact. In other words, such non-proteolytic proteoglycanases depolymerize the glycosaminoglycan chains of the proteoglycan component of the AF and NP.

A number of proteoglycan-degrading enzymes can be used in the treatment of the present invention, including chondroitinase (chondroitin lyase), which depolymerizes the glycosaminoglycans of chondroitin sulfate (particularly chondroitin-4-sulfate and chondroitin-6-sulfate) by the elimination of 1,4-hexosaminidic bonds, hyaluronidase, hyaluronoglucosaminidase, hyaluronoglucuronidase, N-acetylglucosaminidase-, hyaluronate lyase, chondroitin-sulphatase, chondro-4-sulphatase, and chondro-6-sulphatase. A particularly preferred chondroitinase is chondroitinase ABC (chondroitin ABC lyase; EC 4.2.2.4), which is an endo-β-N-acetyl-D-hexosaminidase. Other preferred chondroitinases include chondroitinase AC (chondroitin AC lyase), chondroitinase B (chondroitin B lyase), and chondroitinase C (chondroitin C lyase). As can be seen, a proteoglycan-degrading enzyme includes any glycosidase that can degrade chondroitin sulfate or hyaluronic acid.

The amount of proteoglycan-degrading enzyme used in a method of the present invention is an effective proteoglycan cleaving amount. An effective proteoglycan cleaving amount of a particular proteoglycan-degrading enzyme can be determined by measuring the formation of reaction endproducts over time when the proteoglycan-degrading enzyme is incubated in the presence of its substrate. Thus, for example, one unit (U) of chondroitinase ABC is defined as the amount of enzyme that catalyzes the formation of 1 mmole of unsaturated disaccharide from chondroitin-6-sulfate per minute at 37° C. at pH 8.0. An effective proteoglycan cleaving amount of a proteoglycan-degrading enzyme is in the range of about 0.01 U/disk to about 10 U/disk, preferably from about 0.05 U/disk to about 5 U/disk, and more preferably from about 0.1 U/disk to about 10 U/disk. The amount of proteoglycan-degrading enzyme administered to a host mammal can also be expressed as an amount per unit volume. Thus, an effective proteoglycan cleaving amount of a proteoglycan-degrading enzyme is in the range of about 0.0001 U/mL to about 100 U/mL, preferably from about 0.05 U/mL to about 50 U/mL, and more preferably from about 0.1 U/mL to about 20 U/mL.

A method of the present invention also involves administering to a mammal in need of chemonucleolysis an amount of a growth factor effective for stimulating the formation of a matrix component. An effective proteoglycan synthesizing amount of a growth factor can be administered, or alternatively an effective collagen synthesizing amount of a growth factor can be administered.

A wide variety of growth factors can be used in the present invention. Growth factors are proteins that can activate cellular proliferation and/or differentiation. Many growth factors are pleuripotent and can lead to cell growth and/or differentiation in a variety of cell types. Growth factors useful in the present invention include those growth factors that stimulate matrix synthesis by stimulating the production of proteoglycan and collagen. A suitable growth factor for use in a method of the invention includes any growth factor that has the potential to stimulate matrix synthesis, such as for example, the synthesis of proteoglycan and collagen. Such a growth factor repairs the matrices of the nucleus pulposus and/or annulus fibrosus following chemonucleolysis treatment. Such a growth factor also replenishes the proteoglycan and/or collagen components of NP and/or AF after chemonucleolysis with a proteoglycan-degrading enzyme. Thus, administration of a growth factor restores mechanical strength to the intervertebral disk following chemonucleolysis. In this way, fusion of the intervertebral disk can be delayed or even avoided.

Preferred growth factors include members of the transforming growth factor β family, which family has proliferative effects on many mesenchymal and epithelial cell types. Members of the transforming growth factor β family that are preferred include bone morphogenetic protein 2 (BMP-2); bone morphogenetic protein 4 (BMP-4); and transforming growth factors β-1, β-2, and β-3 (potent keratinocyte growth factors). Other useful members of the transforming growth factor β family include BMP-3, BMP-5, BMP-6, BMP-9, DPP, Vg1, Vgr, 60A protein, GDF-1, GDF-3, GDF-5, GDF-6, GDF-7, CDMP-1, CDMP-2, CDMP-3, BMP-10, BMP-11, BMP-13, BMP-15, Univin, Nodal, Screw, ADMP, Neural, and amino acid sequence variants thereof. Other preferred growth factors include epidermal growth factor (EGF), which induces proliferation of both mesodermal and ectodermal cells, particularly keratinocytes and fibroblasts; platelet-derived growth factor (PDGF), which exerts proliferative effects on mesenchymal cells; fibroblast growth factor (FGF), both acidic and basic; and insulin-like growth factor 1 (IGF-1) and 2 (IGF-2), which mediate the response to growth hormone, particularly in bone growth. Further preferred growth factors include osteogenic proteins. A particularly preferred osteogenic protein is OP-1, also known as bone morphogenetic protein 7 (BMP-7). OP-1 is a member of the transforming growth factor β gene superfamily. It is a 139 amino acid residue long homodimer of MW 36,000. OP-1 induces new bone formation in vivo and promotes the repair of diaphyseal segmental bone defects.

As disclosed in co-pending U.S. application Ser. No. 60/103,161, filed Oct. 6, 1998, and whose disclosure is incorporated herein in its entirety by reference, useful osteogenic proteins include those having an amino acid sequence sharing at least 70% sequence homology or "similarity", and preferably 80% homology, with a reference morphogenic protein selected from the group of naturally-occurring proteins. A candidate amino acid sequence thought to be functionally equivalent to a reference amino acid sequence can be aligned therewith using the method of Needleman et al., *J. Mol. Biol.* 48:443–453 (1970), implemented conveniently by computer programs such as the Align program (DNAstar, Inc.). Internal gaps and amino acid insertions in the candidate sequence are ignored for purposes of calculating the defined relationship, conventionally expressed as a level of amino acid sequence homology or identity, between the candidate and reference sequences.

"Amino acid sequence homology" is understood herein to include both amino acid sequence identity and similarity. Homologous sequences share identical and/or similar amino acid residues, where similar residues are conservative substitutions for, or "allowed point mutations" of, corresponding amino acid residues in an aligned reference sequence. Thus, a candidate polypeptide sequence that shares 70% amino acid homology with a reference sequence is one in which any 70% of the aligned residues are either identical to, or are conservative substitutions of, the corresponding residues in a reference sequence.

As used herein, "conservative substitutions" are residues that are physically or functionally similar to the corresponding reference residues, e.g., that have similar size, shape, electric charge, chemical properties including the ability to form covalent or hydrogen bonds, or the like. Particularly preferred conservative substitutions are those fulfilling the criteria defined for an accepted point mutation in Dayhoff et al. (1978), 5 *Atlas of Protein Sequence and Structure*, Suppl. 3, ch. 22 (pp. 354–352), Natl. Biomed. Res. Found., Washington, D.C. 20007. Examples of conservative substitutions include the substitution of one amino acid for another with similar characteristics, e.g., substitutions within the following groups are well-known: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine. The term "conservative variant" or "conservative variation" also includes the use of a substituted amino acid in place of an unsubstituted parent amino acid in a given polypeptide chain, provided that antibodies having binding specificity for the resulting substituted polypeptide chain also have binding specificity (i.e., "crossreact" or "immunoreact" with) the unsubstituted or parent polypeptide chain.

Useful osteogenically active proteins can also have polypeptide chains with amino acid sequences comprising a sequence encoded by a nucleic acid that hybridizes, under low, medium or high stringency hybridization conditions, to DNA or RNA encoding reference osteogenic sequences, e.g., C-terminal sequences defining the conserved seven cysteine domains of OP-1, OP-2, BMP-2, BMP-4, BMP-5, BMP-6, 60A, GDF-3, GDF-5, GDF-6, GDF-7, CDMP-1, CDMP-2, CDMP-3 and the like. As used herein, high stringent hybridization conditions are defined as hybridization according to known techniques in 40% formamide, 5× SSPE, 5× Denhardt's Solution, and 0.1% SDS at 37° C. overnight, and washing in 0.1× SSPE, 0.1% SDS at 50° C. Standard stringency conditions are well characterized in commercially available, standard molecular cloning texts. See, for example, *Molecular Cloning A Laboratory Manual, 2nd Ed.*, ed. by Sambrook, Fritsch and Maniatis (Cold Spring Harbor Laboratory Press: 1989); DNA Cloning, Volumes I and II (D. N. Glover ed., 1985); *Oligonucleotide Synthesis* (M. J. Gait ed., 1984): *Nucleic Acid Hybridization* (B. D. Hames & S. J. Higgins eds. 1984); and B. Perbal, *A Practical Guide To Molecular Cloning* (1984).

An effective proteoglycan synthesizing amount of a growth factor can be determined by, for example, assaying for the amount of sulfated proteoglycans in a growth factor treated sample using the DMMB dye assay. Häuselmann, et al., *J. Cell. Sci.* 107:17–27 (1994). Alternatively, proteoglycan synthesis can be measured by monitoring the uptake of sulfur-35 ($^{35}$S) by cells in a growth factor treated sample. The proteoglycan synthesizing growth factor can be administered to a host mammal in single or divided daily doses of about 100 μg/disk to about 10 mg/disk daily, preferably about 200 μg/disk to about 1 mg/disk daily and more preferably about 200 μg/disk to about 500 μg/disk. The amount of proteoglycan synthesizing growth factor administered to a host mammal in a single or divided daily dose can also be expressed as an amount per unit volume. Thus, the proteoglycan stimulating growth factor can be administered to a host mammal in single or divided daily doses of about 50 ng/mL to about 5 mg/mL daily, preferably about 200 ng/mL to about 500 μg/mL, and more preferably about 200 ng/mL to about 500 ng/mL. Dosage unit compositions can contain such amounts or submultiples thereof to make up the daily dose. A suitable dose can be administered in multiple sub-doses per day. Multiple doses per day can also increase the total daily dose, should such dosing be desired by the person prescribing the drug.

The dosage regimen for treating a disease condition with a compound and/or composition useful in this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed can vary widely and therefore can deviate from the preferred dosage regimen set forth above.

It is contemplated that the growth factors can be administered either singly or in a "cocktail" comprising more than one growth factor. For example, a mixture of OP-1 and BMP-4 can be administered simultaneously to provide an effective proteoglycan synthesizing amount of growth factor. To facilitate the simultaneous administration of a cocktail of growth factors, the growth factor cocktail can be formulated as a pharmaceutical composition containing conventional pharmaceutically acceptable carriers and vehicles, as described elsewhere herein.

It is also contemplated that the effective proteoglycan cleaving amount of a proteoglycan-degrading enzyme and the effective proteoglycan synthesizing amount of a growth factor can be administered simultaneously to a mammal in need of chemonucleolysis. The effect of a proteoglycan-degrading enzyme such as chondroitinase ABC is maximal within 24 hours after injection, although approximately 2% of the administered amount can still be found in the NP 10 days post-injection. Takahashi et al., Spine 21:2405–2411 (1996). Growth factors typically require at least 24 hours to induce an effect through the growth factor cascade. OP-1, for example, exhibits its maximal effect on the metabolism of chondrocytes approximately 72 hours after administration. To facilitate the simultaneous administration of a proteoglycan-degrading enzyme and a growth factor, the combination of these two compounds can be prepared as a composition of matter comprising a proteoglycan-degrading enzyme and a growth factor. This combination can be formulated as a pharmaceutical composition containing conventional pharmaceutically acceptable carriers and vehicles, as described elsewhere herein.

The effective proteoglycan cleaving amount of a proteoglycan-degrading enzyme and the effective proteoglycan synthesizing amount of a growth factor can also be administered sequentially to a mammal in need of chemonucleolysis. The proteoglycan-degrading enzyme administration can be followed with growth factor administration at any time point after the administration of the proteoglycan-degrading enzyme, preferably within about 24 hours after completion of the administration of the proteoglycan-degrading enzyme. However, it is to be understood that growth factor administration can be repeated on multiple occasions after the administration of the proteoglycan-degrading enzyme.

A mammal in need of chemonucleolysis can receive one or more administrations of proteoglycan-degrading enzyme until the desired clinical outcome is achieved. Thus, for example, multiple doses of proteoglycan-degrading enzyme can be administered until there is a reduction in reported pain, or until diagnostic analyses, such as by MRI, demonstrate that the degree of herniation of the intervertebral disk has lessened. Growth factor administration can then proceed thereafter, and can also utilize multiple administrations until the desired clinical outcome is achieved. For example, repair of the AF and NP following administration of a growth factor can be confirmed by diagnostic analyses, such as by MRI. The skilled practitioner will appreciate that the administration of growth factor following administration of proteoglycan-degrading enzyme is controlled so as to prevent recurrence of symptomology or to prevent recurrence of the herniation.

The administration of a proteoglycan-degrading enzyme is preferably performed by direct injection into the intervertebral disk space. Similarly, the administration of a growth factor is preferably done by direct injection into the intervertebral disk space. However, it is also contemplated that the growth factor can be administered by continuous infusion into the intervertebral space using, for example, an implantable or external continuous infusion pump fitted with an appropriate intervertebral catheter.

The treatment method of the invention is used for treating a host mammal such as a mouse, rat, rabbit, dog, horse, primate such as a monkey, chimpanzee or human that has a condition requiring the treatment method.

A compound useful in the present invention can be formulated as a pharmaceutical composition. Such a composition can then be administered parenterally in dosage unit formulations containing conventional nontoxic pharmaceutically acceptable carriers and vehicles as desired. The term parenteral as used herein includes intervertebral injections, or local infusion techniques. Formulation of drugs is discussed in, for example, Hoover, John E. (ed.), Remington's Pharmaceutical Sciences (18$^{th}$ Edition), Mack Publishing Co., Easton, Pa., 1990 and Liberman, H. A. and Lachman, L., Eds., Pharmaceutical Dosage Forms, Marcel Decker, New York, N.Y., 1980. As discussed elsewhere herein, the administration of a proteoglycan-degrading enzyme or growth factor of the invention is typically by direct local injection or local infusion into the intervertebral disk space.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and nonionic detergents, polyethylene glycols can be used. Mixtures of solvents and wetting agents such as those discussed above are also useful.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents used in formulations for oral administration, as is well known in the art. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

A compound useful in the present invention can also be formulated into liposomes, as discussed in Hoover, John E. (ed.), Remington's Pharmaceutical Sciences (18$^{th}$ Edition), Mack Publishing Co., Easton, Pa., 1990, p. 1691. Liposomes are formed by dispersing phospholipids in an aqueous medium. Water- or lipid-soluble substances can be entrapped in the aqueous space within a liposome, or within the lipid bilayers of the liposome, respectively. Thus, a growth factor can be formulated into liposomes for use in a method of the invention using techniques that are well known in the art.

As noted above, the amount of active ingredient that can be combined with the carrier materials to produce a single dosage form varies depending upon the mammalian host treated and the particular mode of administration.

In another embodiment, the present invention contemplates a kit comprising a proteoglycan-degrading enzyme and a growth factor. Such a kit contains a proteoglycan-degrading enzyme of the invention packaged together with a growth factor of the invention. The kit is packaged in a conventional manner, as is well known in the art.

A kit of the invention preferably comprises a vessel containing a proteoglycan-degrading enzyme and a vessel containing a growth factor. Such a vessel can be a glass vial or container, a plastic vial or container, or other suitable container, as is well known in the art. In another preferred embodiment, the kit comprises a vessel containing a proteoglycan-degrading enzyme and a growth factor. Such a kit is especially suited for simultaneous administration of a proteoglycan-degrading enzyme and a growth factor according to a method of the invention.

Any of the above-described kits optionally include instructions for using the proteoglycan-degrading enzyme and the growth factor in chemonucleolysis. For example, the instructions provide details on using the components of the kit in a method of the present invention.

The following examples are offered to further illustrate, but not limit the present invention.

EXAMPLE 1

Upregulation of Extracellular Matrix Metabolism by Rabbit Annulus Fibrosus and Nucleus Pulposus Cells Using Recombinant Osteogenic Protein-1

Materials and Methods

Cell Culture: Lumbar intervertebral disks (IVDs) were aseptically dissected from the spine of New Zealand white rabbits after euthanasia. The NP and AF were separated by blunt dissection and separately pooled. Cells were released from each tissue by sequential enzyme digestion (Pronase 1 hour, and Collagenase P and DNAase II for 16 hours) and the isolated cells encapsulated in 1.2% low-viscosity alginate at 2 million/mL as previously described. Chiba, K. et al., *Spine* 22:2885 (1997). The cultures were maintained in DMEM/F12 plus 10% FBS with a daily change of media.

Measurement of the Effect Of rhOP-1 on Cell Proliferation and PG and Collagen Synthesis: On day 7 of culture, the cells in alginate were incubated in the presence of various concentrations of the growth factor recombinant human OP-1 (rhOP-1) for 72 hours. The culture was also treated as follows:

(1) To measure cell proliferation, MTT (5%) was added to the medium of these cultures during the last 60 minutes. After dissolving the beads with calcium chelating agents, the cells were lysed, centrifuged and the absorbance of the supernatant at 550 nm was measured. Mosmann, T. J., *Immunol. Methods* 65:55 (1984).

(2) To measure PG synthesis, $^{35}$S-sulfate (20 μCi/mL) was added to the medium during the last 4 hours of the 72 hour period of incubation in the presence of rhOP-1. After removing the medium, the beads were dissolved and the two compartments [cell-associated matrix (CM) and further removed matrix (FRM)] separated by mild centrifugation. Mok, S. S. et al., *J. Biol. Chem.* 269:33021 (1994). Each fraction was solubilized with papain and incorporation of $^{35}$S-sulfate determined using a rapid filtration assay to recover $^{35}$S-PGs precipitated by alcian blue. Masuda, K. et al., *Anal. Biochem.* 217:167 (1994).

(3) To measure collagen synthesis, the cultures were labeled with $^{3}$H-proline in DMEM+2% FBS during the last 16 hours of treatment with rhOP-1. After removing the medium, collagen in the beads was extracted. Each extract was dialyzed against water followed by pepsinization and dialysis. $^{3}$H-hydroxyproline (as a measure of $^{3}$H-collagen) was quantified after acid hydrolysis followed by separation of the radiolabeled imino acids by HPLC on a cation exchange column. Häuselmann, H. J. et al., *J. Cell Sci.* 107:17 (1994). PG and Collagen Accumulation in Alginate Beads: The cells were cultured with DMEM/F12+10% FBS in the continuous absence or presence of rhOP-1 (100 ng/mL). At various time points, the beads were treated with papain at 60° C. and the papain digests were analyzed for contents of PG (by the DMMB procedure), hydroxyproline (using reverse-phase HPLC after acid hydrolysis and PITC labeling) and DNA (by a fluorometric method using Hoechst 33258 dye). Chiba, K. et al., *Spine* 22:2885 (1997).

Statistical Analyses: Statistical analyses were performed by one way ANOVA with Fisher's PLSD test as a post hoc test.

Results

Cell Proliferation and DNA Content: The MTT analyses revealed that rhOP-1 had a significant mitogenic effect at high concentrations only (AF: 100 and 200 ng/mL, P<0.01; NP: 100 ng/mL, P<0.01). Treatment with rhOP-1 (100 ng/mL) was associated at all time points studied with an increase in the total DNA content of AF cultures (% of control: day 3=135%; day 6=134%; Day 11=126%; Day 14=126%) but not of NF cultures (p>0.05).

PG Synthesis: rhOP-1-treatment resulted in a significant dose-dependent increase in PG synthesis by both the AF and NP cultures maintained in the presence of 10% FBS (see FIG. 1, p<0.001). The rate of PG synthesis remained significantly elevated in both AF and NP cultures when expressed per μg DNA: NP cells were more responsive than AF cells to rhOP-1 (rate of synthesis as % of control: AF=230%; NP=460%). It should be noted that in the presence or absence of rhOP-1, AF cells produced more $^{35}$S-PGs than NP cells.

Figure 11:
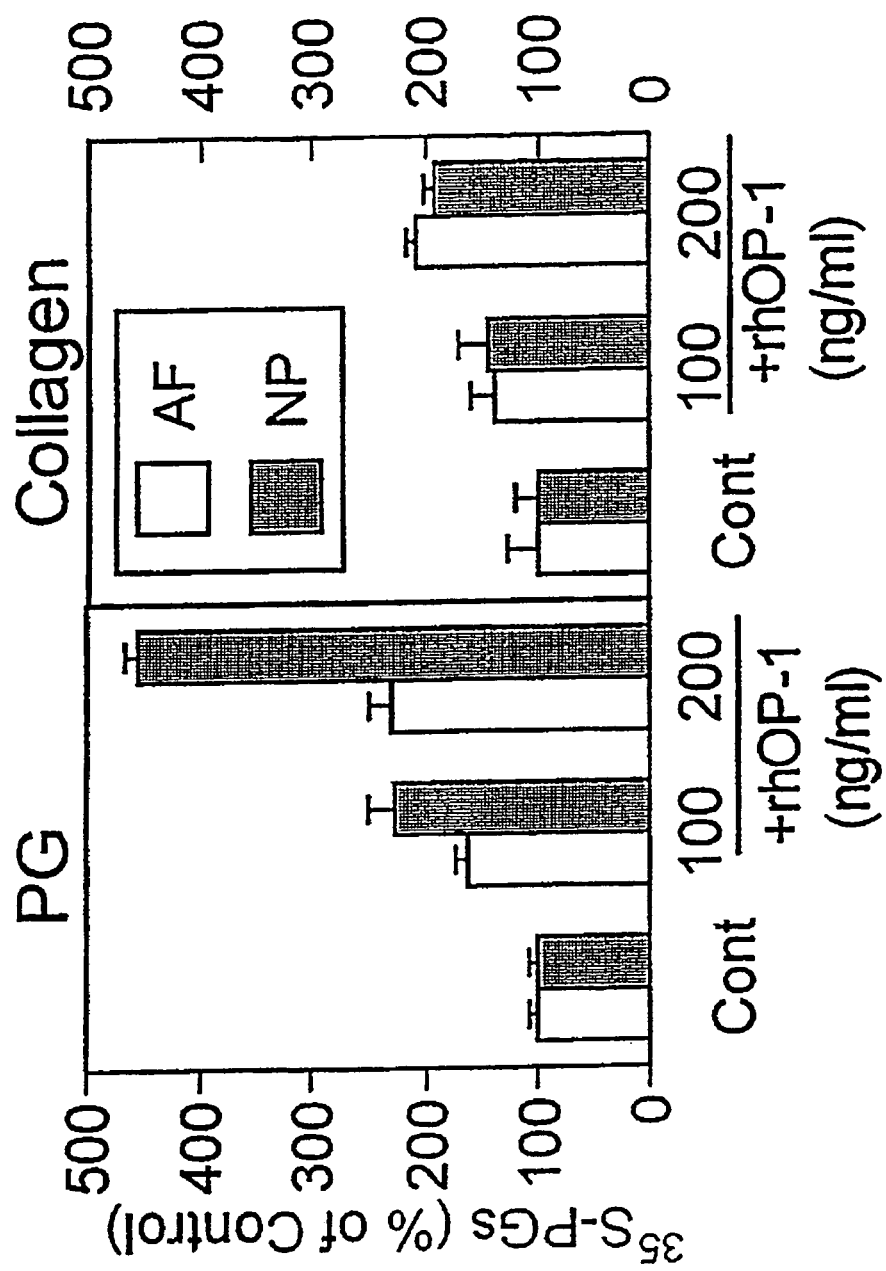
FIG. 11 illustrates the effects of recombinant human OP-1 ("rhOP-1") on proteoglycan ("PGs") and collagen synthesis in the annulus fibrosus ("AF"; open bars) and the nucleus pulposus ("NP", filled bars). In the control ("Cont"), no rhOP-1 was added. PG synthesis is expressed as the percentage of $^{35}$S-PGs synthesized when 100 ng/ml rhOP-1 or 200 ng/ml rhOP-1 was added, compared to the control. Collagen synthesis is expressed as the percentage of $^3$H-hydroxyproline synthesized when 100 ng/ml rhOP-1 or 200 ng/ml rhOP-1 was added, compared to the control. The data are all presented with standard error bars.

Collagen Synthesis: rhOP-1 stimulated collagen synthesis by both NP cells and AF cells in a dose-dependent manner (see FIG. 11, P<0.01), but the magnitude of the response was less marked than in the case of PG synthesis (see FIG. 11, P<0.01). Although rhOP-1 had a significant mitogenic effect at high doses, the rate of collagen synthesis remained significantly elevated when expressed per μg DNA. As was observed in the case of PG synthesis, AF cells produced under all conditions more $^{3}$H-collagen than NP cells.

Matrix Accumulation: The addition of rhOP1 at 100 ng/ml to the medium resulted in a marked increase in the total content of PG and collagen in both the AF and NP beads. In both the AF and NP, this increase was only minor during the first week, but dramatic during the second week of culture with rhOP-1 (data not shown). This delay was especially evident in the case of collagen accumulation.

Discussion

These data show the ability of growth factor rhOP-1 to stimulate the metabolism of both AF and NP cells. Although this morphogenetic protein only had a moderate mitogenic effect upon the cells, it stimulated them to synthesize PGs and collagen at faster rates than in the presence of 10% FBS alone. The stimulation of PG synthesis was especially great in the case of the NP cells that are normally much less effective than articular chondrocytes or AF cells to reform a cell-associated matrix in vitro. Interestingly, the stimulatory effects of rhOP-1 on PG synthesis were more apparent than those on collagen metabolism.

In human disks, the PG content of the NP decreases with age and drops rapidly in degenerative disk disease (Gower, W. E. et al., *J. Bone Joint Surg.* 51-A: 1154 (1969), when longitudinal and circular tears, that reflect the disruption of the collagen network structure, are often observed by MRI. The data demonstrate that growth factor rhOP-1 is useful as a therapeutic agent in promoting synthesis and repair of the matrix of both the AF and NP elements of degenerating human IVDs by increasing the synthesis of proteoglycan and collagen.

EXAMPLE 2

Osteogenic Protein-1 Stimulation of Proteoglycan Synthesis by Nucleus Pulposus and Annulus Fibrosus Following Chondroitinase ABC-Induced Chemonucleolysis Treatment Materials and Methods Lumbar spines were removed en bloc, under aseptic conditions, from adolescent New Zealand white rabbits weighing 3–4.0 Kg (IACUC approval # 94-053). The lumbar disks were dissected and the NP separated in each case from the AF. Cells were separately isolated from the two tissues by sequential enzyme digestion and resuspended in 1.2% low viscosity sterile alginate at 2 million/mL. Chiba, K., et al., *Spine* 22:2885–2893 (1997). Beads were formed by expressing this solution dropwise, through a 22 gauge needle, into a 102 mM $CaCl_2$ solution. The NP and AF cells in the beads were maintained in batch culture in DMEM/F-12 medium containing 10% FBS, 25 μg/mL ascorbate and 50 μg/mL gentamicin. This complete medium was changed daily throughout the study.

On day 14 of culture, beads were divided into three groups. The first comprised beads cultured for an additional 12 days in complete medium (Group 1—control cultures). The beads in the other two groups were first cultured for 2 hours in the presence of the proteoglycan-degrading enzyme chondroitinase ABC (C-ABC) (0.1 U/mL), to deplete PGs from the matrix, followed by 3×30 minute washes before culturing the beads for the next 12 days in complete medium either in the presence (Group 2) or absence (Group 3) of growth factor OP-1 at 200 ng/mL.

At various times, the matrix in the beads was solubilized by digestion with papain at 60° C. The digests were analyzed for content of DNA, using the Hoechst 33258 dye and fluorometry, and sulfated PGs, using the DMMB dye assay. Hauselmann, H. J. et al., *J. Cell Sci.* 107:17–27 (1994). For each time point, all analyses of NP and AF beads were performed on 3 sets of 9 beads each. Statistical analyses were performed by one way ANOVA with Fisher's PLSD test as a post hoc test.

Results

Figure 2:
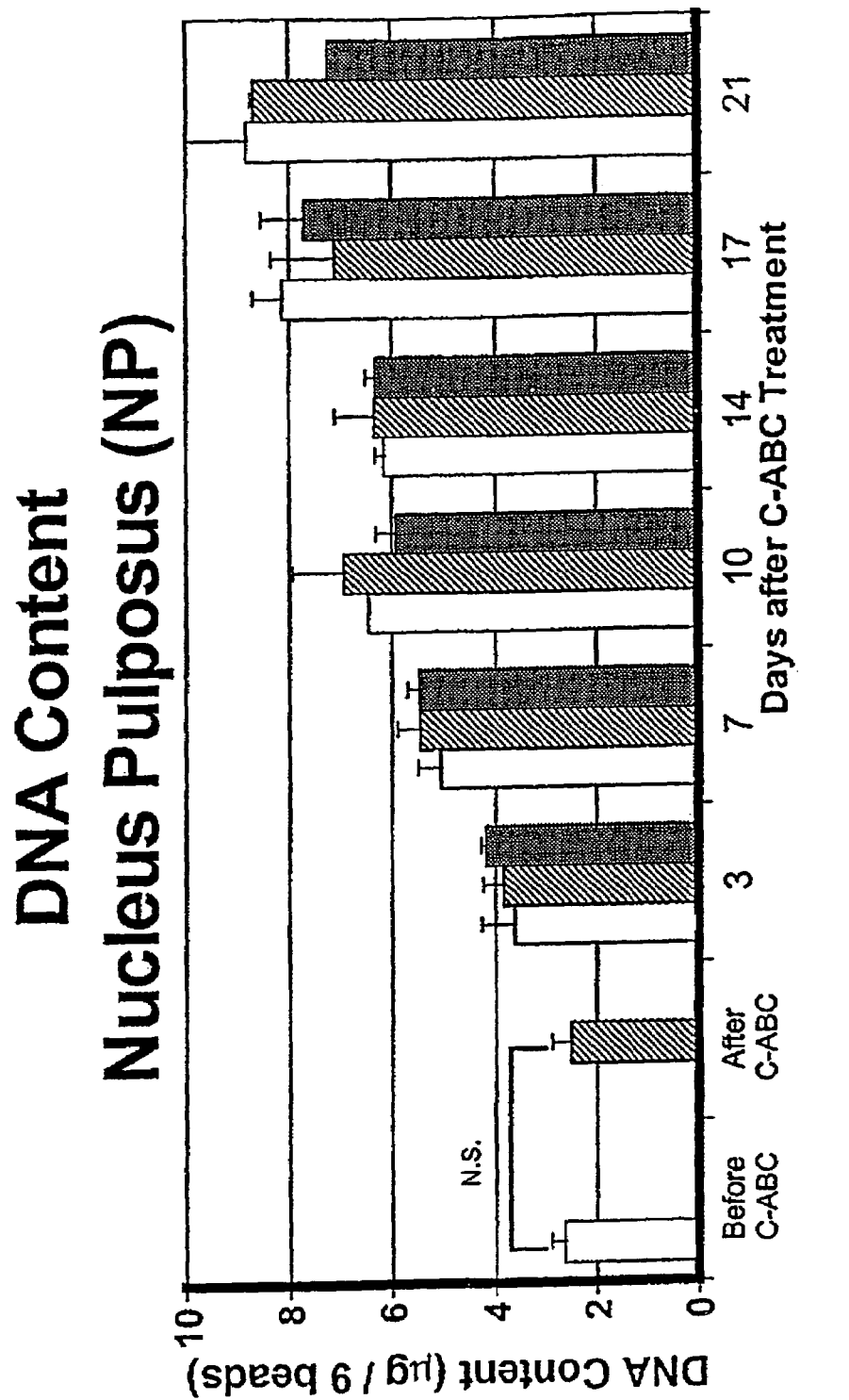
FIG. 2 illustrates the effects of OP-1 on the DNA content, in micrograms per 9 alginate beads, of the nucleus pulposus ("NP") treated with chondroitinase ABC ("C-ABC"). The open bars represent data for cells not treated with C-ABC or OP-1 ("C-ABC(−), OP-1(−)"). The hatched bars represent data for cells treated with C-ABC only ("C-ABC(+), OP-1(−)"). The filled bars represent data for cells treated with both C-ABC and OP-1("C-ABC(+), OP-1(+)"). The data are all presented with standard error bars. "N.S." indicates that the difference in DNA content in the NP before and after C-ABC treatment at time zero is not significant.
Figure 3:
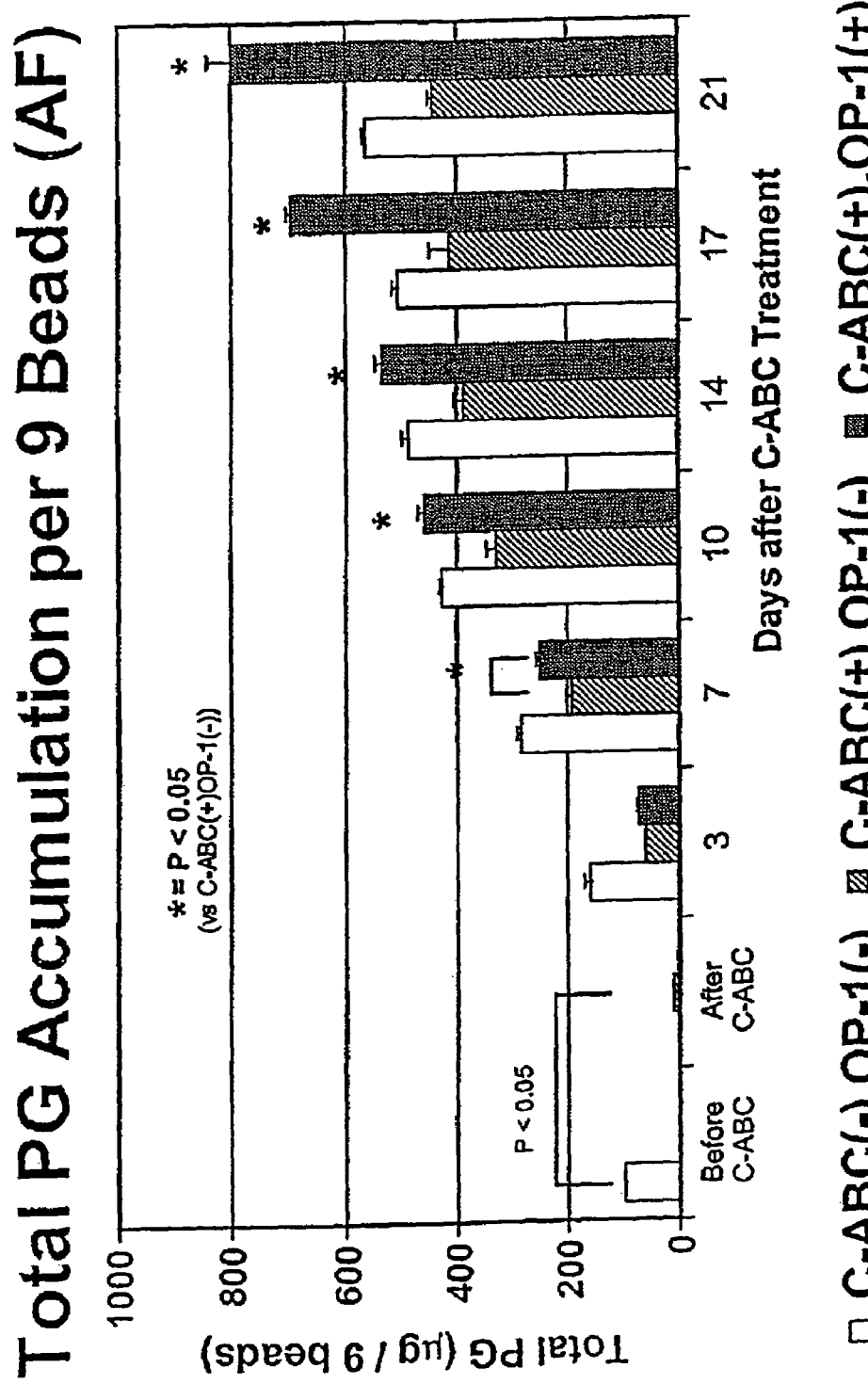
FIG. 3 illustrates the effects of OP-1 on total proteoglycan ("PG") accumulation, expressed as micrograms per 9 alginate beads, of the annulus fibrosus ("AF") treated with chondroitinase ABC ("C-ABC"). The open bars represent data for cells not treated with C-ABC or OP-1 ("C-ABC(−), OP1(−)"). The hatched bars represent data for cells treated with C-ABC only ("C-ABC(+), OP-1(−)"). The filled bars represent data for cells treated with both C-ABC and OP-1 ("C-ABC(+), OP-1(+)"). The data are all presented with standard error bars. At time zero, the difference in total PG before and after C-ABC treatment is statistically significant at $p<0.05$. The * represents statistically significant differences at $p<0.05$ when C-ABC(+), OP-1(+) is compared to C-ABC(+), OP-1(−) at 7, 10, 14, 17 and 21 days after C-ABC treatment.
Figure 4:
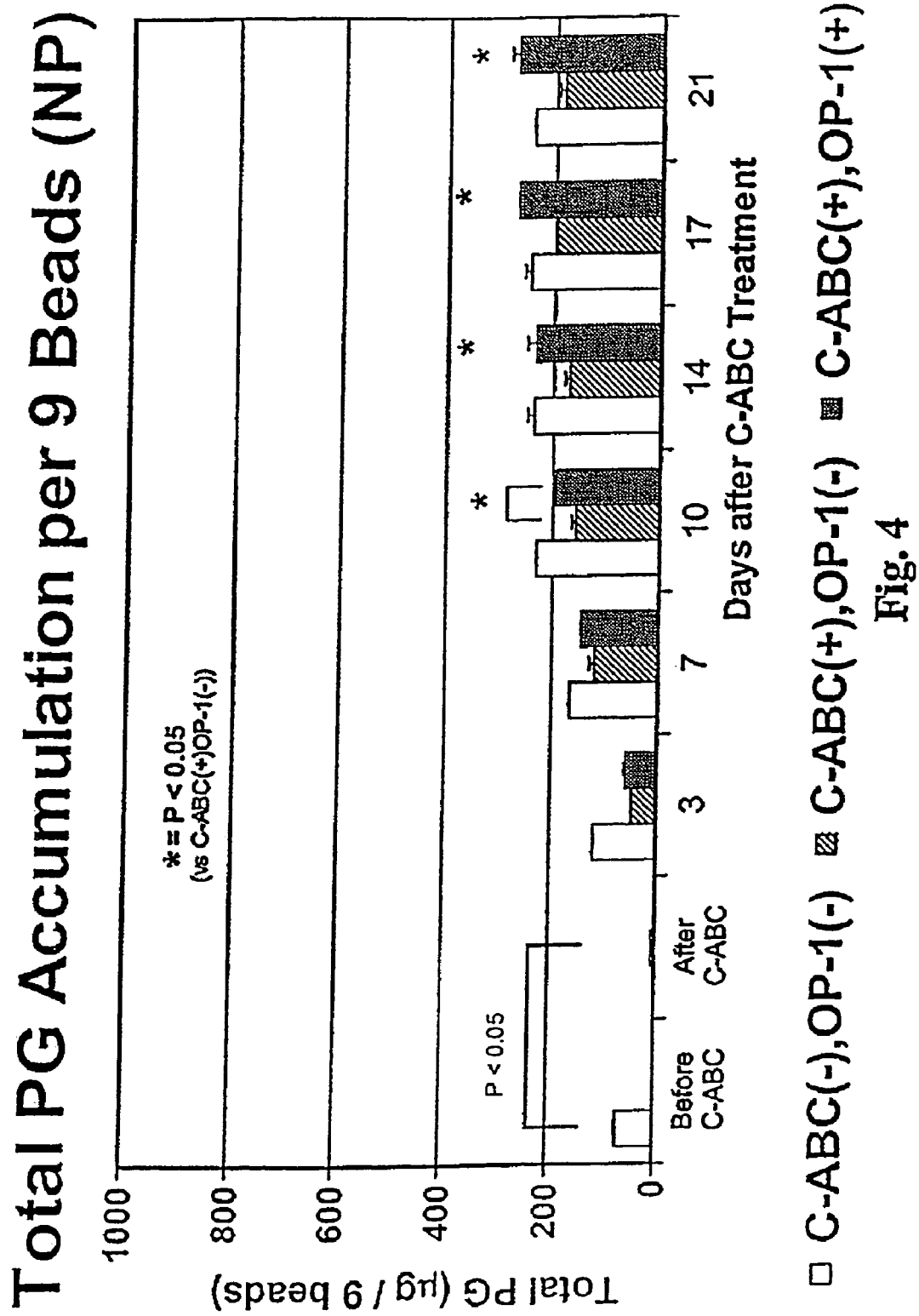
FIG. 4 illustrates the effects of OP-1 on total proteoglycan ("PG") accumulation, expressed as micrograms per 9 alginate beads, of the nucleus pulposus ("NP") treated with chondroitinase ABC ("C-ABC"). The open bars represent data for cells not treated with C-ABC or OP-1("C-ABC(−), OP-1(−)"). The hatched bars represent data for cells treated with C-ABC only ("C-ABC(+), OP-1(−)"). The filled bars represent data for cells treated with both C-ABC and OP-1 ("C-ABC(+), OP-1(+)"). The data are all presented with standard error bars. At time zero, the difference in total PG before and after C-ABC treatment is statistically significant at $p<0.05$. The * represents statistically significant differences at $p<0.05$ when C-ABC(+), OP-1(+) is compared to C-ABC(+), OP-1(−) at 10, 14, 17 and 21 days after C-ABC treatment.
Figure 5:
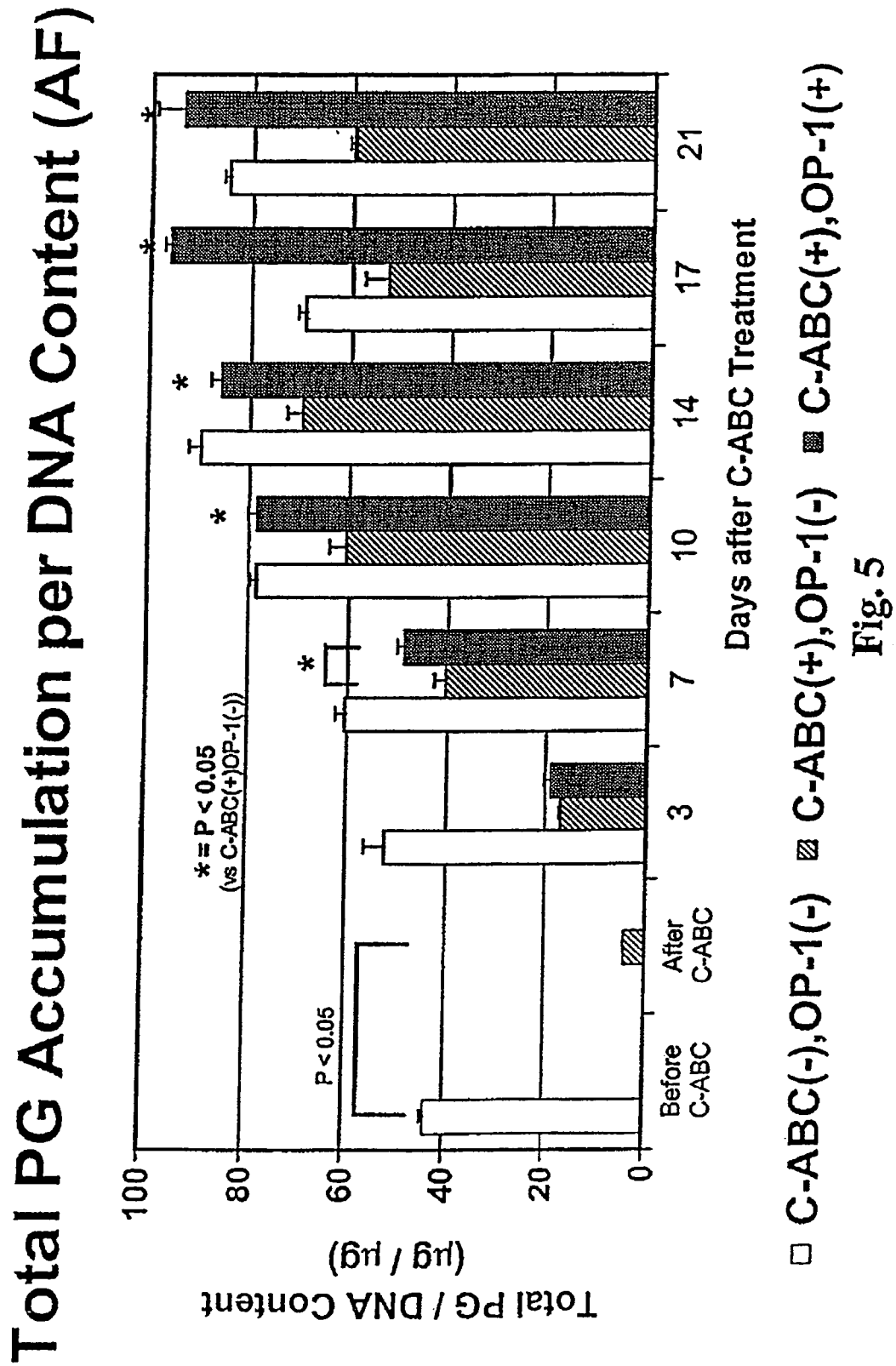
FIG. 5 illustrates the effects of OP-1 on total proteoglycan ("PG") accumulation, expressed as micrograms PGs per microgram DNA, of the annulus fibrosus ("AF") treated with chondroitinase ABC ("C-ABC"). The open bars represent data for cells not treated with C-ABC or OP-1 ("C-ABC(−), OP-1(−)"). The hatched bars represent data for cells treated with C-ABC only ("C-ABC(+), OP-1(−)"). The filled bars represent data for cells treated with both C-ABC and OP-1 ("C-ABC(+), OP-1(+)"). The data are all presented with standard error bars. At time zero, the difference in total PG per DNA content before and after C-ABC treatment is statistically significant at $p<0.05$. The * represents statistically significant differences at $p<0.05$ when C-ABC(+), OP-1(+) is compared to C-ABC(+), OP-1(−) at 7, 10, 14, 17 and 21 days after C-ABC treatment.
Figure 6:
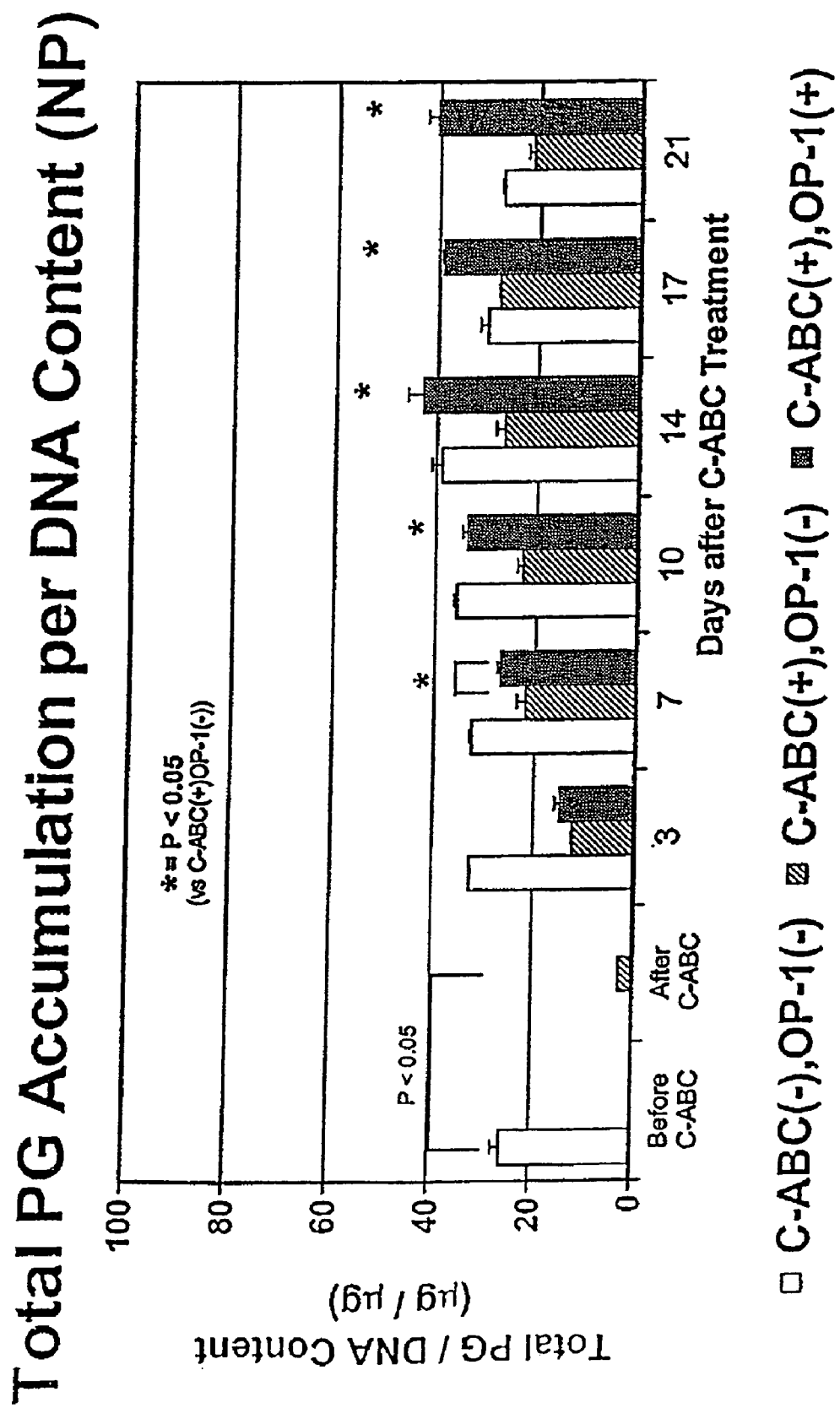
FIG. 6 illustrates the effects of OP-1 on total proteoglycan ("PG") accumulation, expressed as micrograms PGs per microgram DNA, of the nucleus pulposus ("NP") treated with chondroitinase ABC ("C-ABC"). The open bars represent data for cells not treated with C-ABC or OP-1 ("C-ABC(−), OP-1(−)"). The hatched bars represent data for cells treated with C-ABC only ("C-ABC(+), OP-1(−)"). The filled bars represent data for cells treated with both C-ABC and OP-1 ("C-ABC(+), OP-1(+)"). The data are all presented with standard error bars. At time zero, the difference in total PG accumulation per DNA content before and after C-ABC treatment is statistically significant at $p<0.05$. The * represents statistically significant differences at $p<0.05$ when C-ABC(+), OP-1(+) is compared to C-ABC(+), OP-1(−) at 7, 10, 14, 17 and 21 days after C-ABC treatment.
Figure 7:
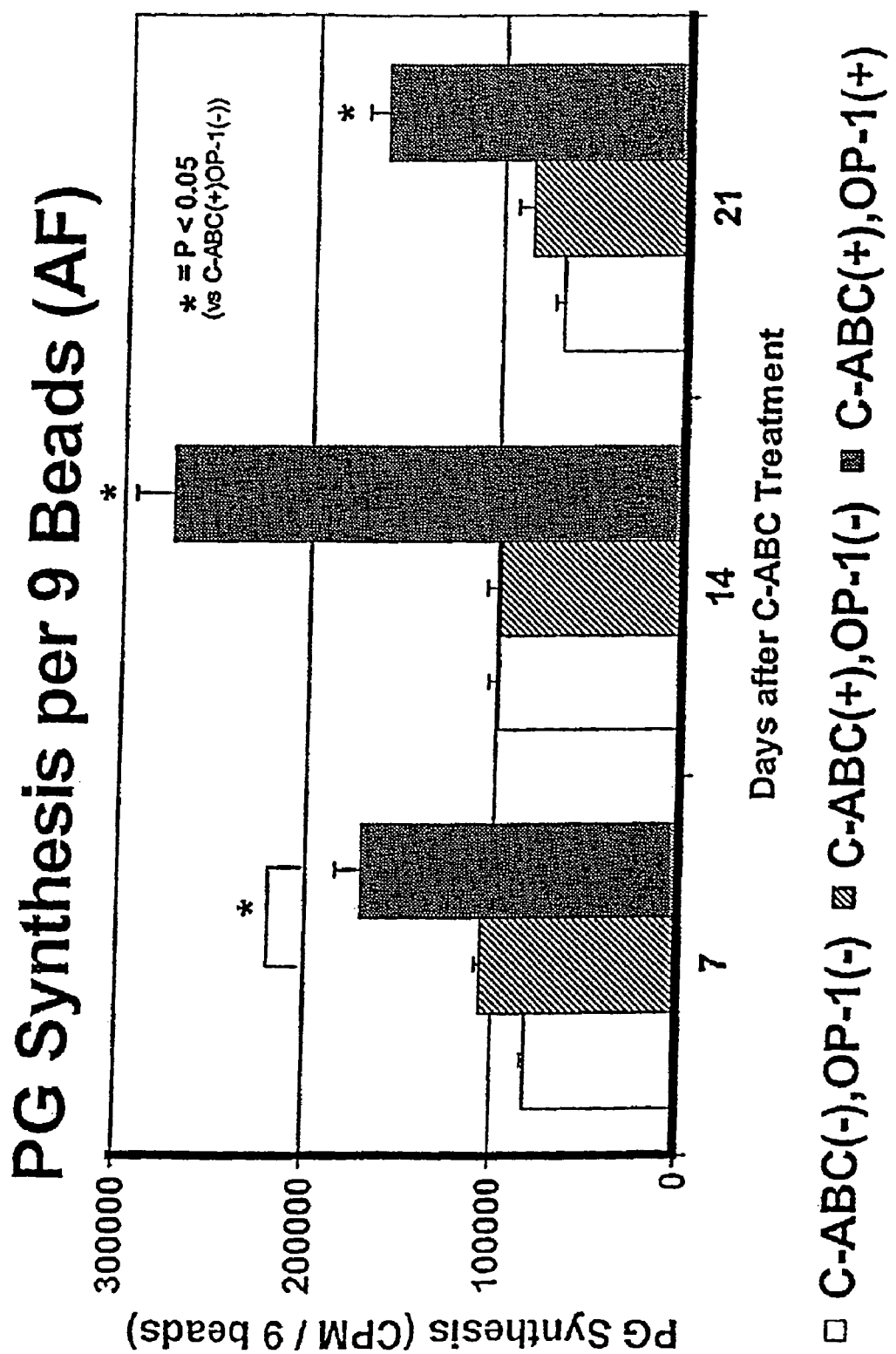
FIG. 7 illustrates the effects of OP-1 on proteoglycan ("PG") synthesis, expressed as counts per minute ("CPM") per 9 alginate beads, of the annulus fibrosus ("AF") treated with chondroitinase ABC ("C-ABC"). The open bars represent data for cells not treated with C-ABC or OP-1 ("C-ABC(−), OP-1(−)"). The hatched bars represent data for cells treated with C-ABC only ("C-ABC(+), OP-1(−)"). The filled bars represent data for cells treated with both C-ABC and OP-1 ("C-ABC(+), OP-1(+)"). The data are all presented with standard error bars. The * represents statistically significant differences at $p<0.05$ when C-ABC(+), OP-1(+) is compared to C-ABC(+), OP-1(−) at 7, 14 and 21 days after C-ABC treatment.
Figure 8:
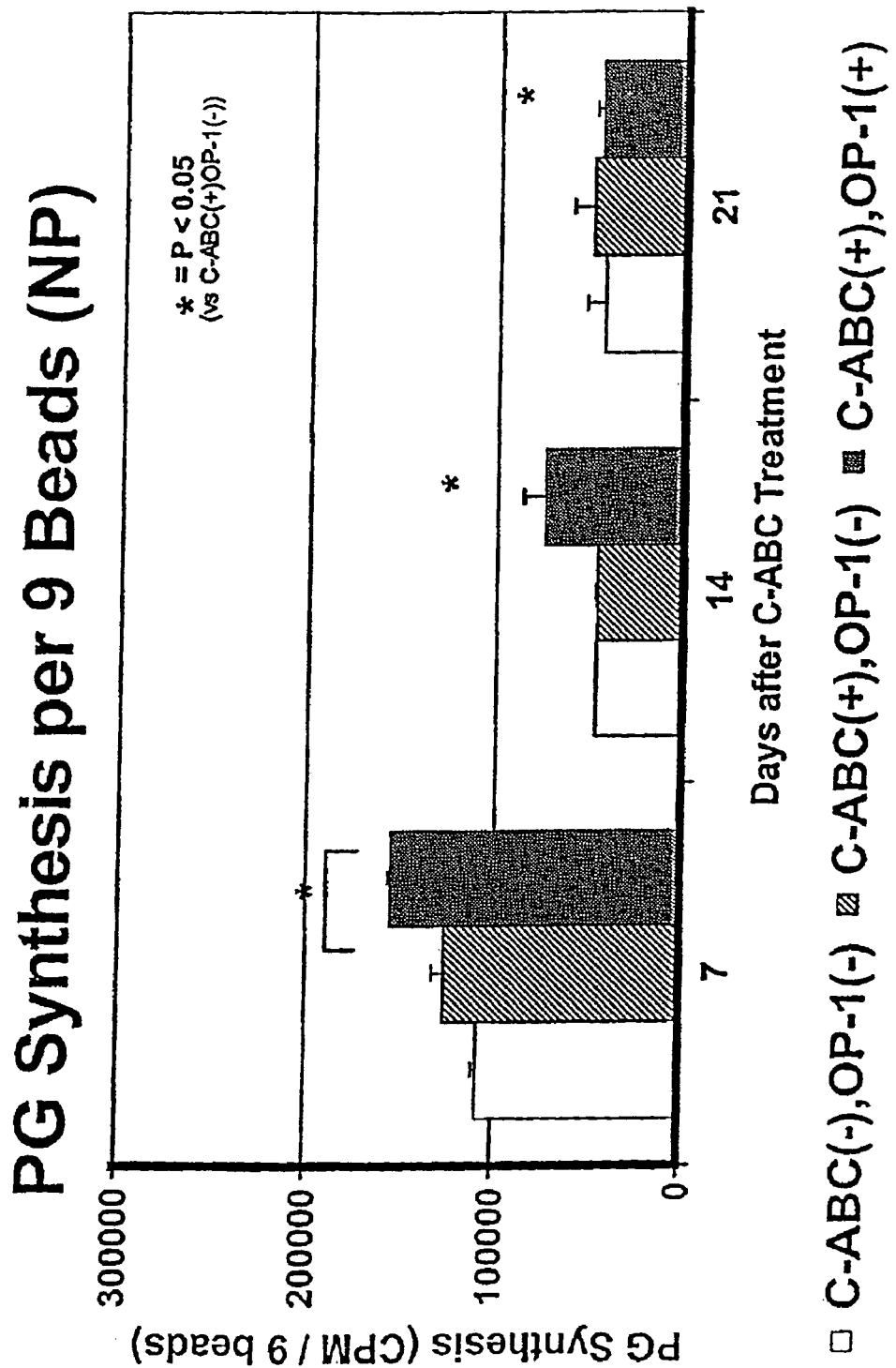
FIG. 8 illustrates the effects of OP-1 on proteoglycan ("PG") synthesis, expressed as counts per minute ("CPM") per 9 alginate beads, of the nucleus pulposus ("NP") treated with chondroitinase ABC ("C-ABC"). The open bars represent data for cells not treated with C-ABC or OP-1 ("C-ABC(−), OP-1(−)"). The hatched bars represent data for cells treated with C-ABC only ("C-ABC(+), OP-1 (−)"). The filled bars represent data for cells treated with both C-ABC and OP-1 ("C-ABC(+), OP-1(+)"). The data are all presented with standard error bars. The * represents statistically significant differences at $p<0.05$ when C-ABC(+), OP-1(+) is compared to C-ABC(+), OP-1(−) at 7, 14 and 21 days after C-ABC treatment.
Figure 9:
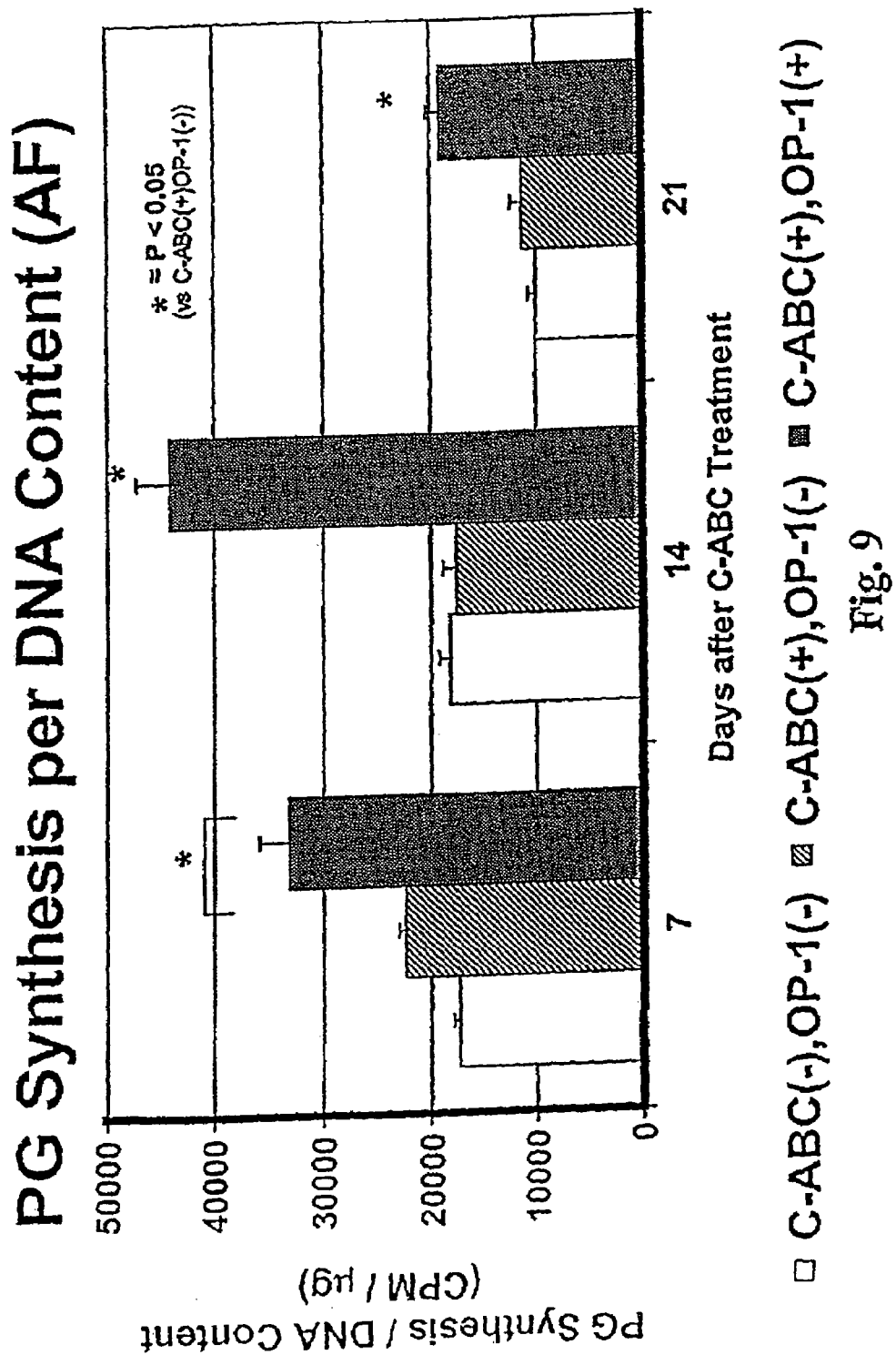
FIG. 9 illustrates the effects of OP-1 on proteoglycan ("PG") synthesis, expressed as counts per minute ("CPM") per microgram of DNA, of the annulus fibrosus ("AF") treated with chondroitinase ABC ("C-ABC"). The open bars represent data for cells not treated with C-ABC or OP-1 ("C-ABC(−), OP-1(−)"). The hatched bars represent data for cells treated with C-ABC only ("C-ABC(+), OP-1(−)"). The filled bars represent data for cells treated with both C-ABC and OP-1 ("C-ABC(+), OP-1(+)"). The data are all presented with standard error bars. The * represents statistically significant differences at $p<0.05$ when C-ABC(+), OP-1(+) is compared to C-ABC(+), OP-1(−) at 7, 14 and 21 days after C-ABC treatment.
Figure 10:
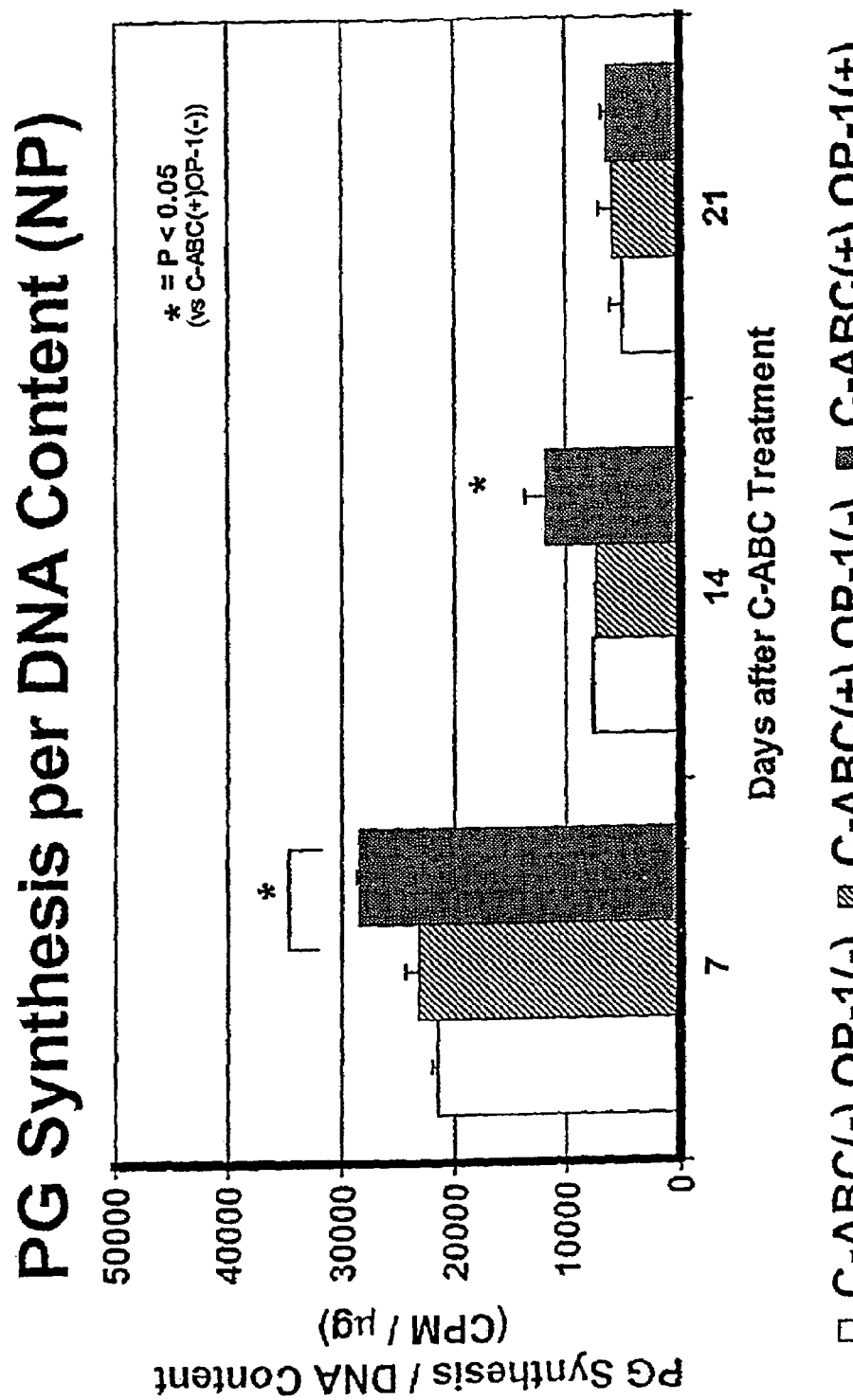
FIG. 10 illustrates the effects of OP-1 on proteoglycan ("PG") synthesis, expressed as counts per minute ("CPM") per microgram of DNA, of the nucleus pulposus ("NP") treated with chondroitinase ABC ("C-ABC"). The open bars represent data for cells not treated with C-ABC or OP-1 ("C-ABC(−), OP-1(−)"). The hatched bars represent data for cells treated with C-ABC only ("C-ABC(+), OP-1(−)"). The filled bars represent data for cells treated with both C-ABC and OP-1 ("C-ABC(+), OP-1(+)"). The data are all presented with standard error bars. The * represents statistically significant differences at $p<0.05$ when C-ABC(+), OP-1(+) is compared to C-ABC(+), OP-1(−) at 7 and 14 days after C-ABC treatment.

The DNA content did not decrease during the treatment of NP or AF cells with C-ABC. DNA content rose moderately in all groups of NP and AF cells during the next nine days before reaching a plateau. Although the increase was not as pronounced in NP and AF beads cultured with OP-1, this difference was not statistically significant. FIGS. 1 and 2.

Figure 12:
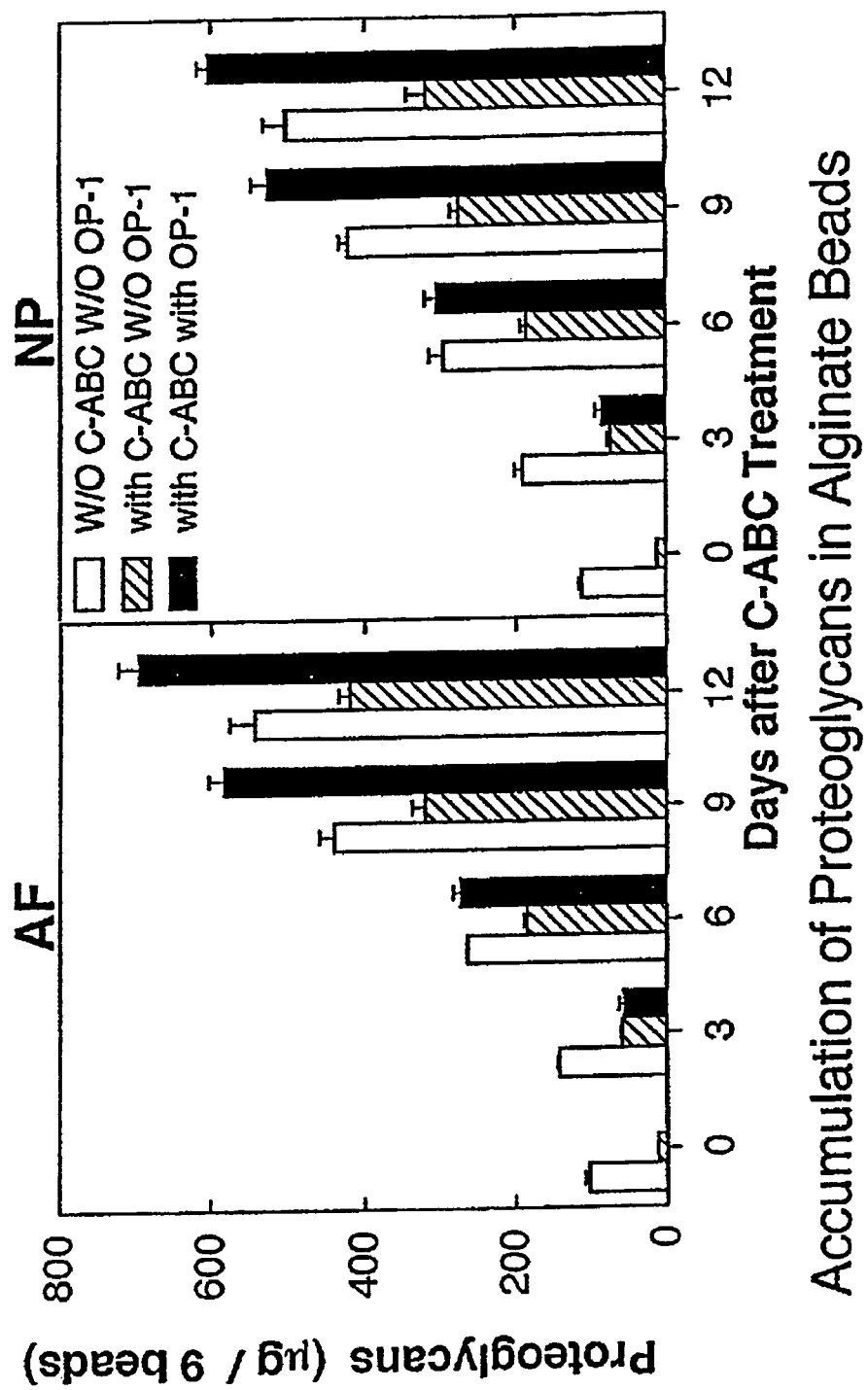
FIG. 12 represents replicate studies illustrating the effects of OP-1 on accumulation of proteoglycans in the annulus fibrosus ("AF", left panel) and nucleus pulposus ("NP", right panel), expressed as micrograms per 9 alginate beads, following chondroitinase ABC ("C-ABC") treatment. The open bars represent data for cells not treated with C-ABC or OP-1 ("W/O C-ABC W/O OP-1"). The hatched bars represent data for cells treated with C-ABC only ("with C-ABC W/O OP—I"). The filled bars represent data for cells treated with both C-ABC and OP-1 ("with C-ABC, with OP—I"). The data are all presented with standard error bars.

Similar observations and conclusions were drawn when PG contents were expressed per bead or per μg DNA. FIGS. 3–10, 12. Consequently, all values for PG contents are reported here only as μg PG per 9 beads. As shown in FIG. 12, the sulfated PG contents of the NP and AF beads not exposed to C-ABC increased progressively over the time of culture. Treatment with C-ABC caused the PG content to drop by more than 85% in both NP and AF beads. Although matrix recovery was clearly evident in both NP and AF beads returned to complete medium without OP-1, the matrix thus formed never reached the PG content seen in beads not treated with C-ABC.

OP-1 at 200 ng/mL appeared to have no significant effect upon matrix accumulation during the first 3 days after treatment with C-ABC. In marked contrast, between days 3 and 6, both NP and AF cells exposed to OP-1 reestablished a matrix as rich in sulfated PGs as that of control cells not exposed to C-ABC. At later times, OP-1 continued to exert its stimulatory effect upon the C-ABC-treated cells: the PG contents reached values that were significantly higher than those not only of the C-ABC-treated cells not exposed to OP-1 but also of the control cells ($P<0.01$). FIG. 12.

Discussion

Theses data demonstrate the effectiveness of growth factor OP-1 in stimulating matrix repair by NP and AF cells after their matrix had been nearly totally depleted of sulfated glycosaminoglycans by a proteoglycan-degrading enzyme. The results are unexpected for several reasons. First, the data show that NP and AF cells are as responsive as articular chondrocytes to OP-1-induced stimulation of PG synthesis. While not wishing to be bound by theory, because OP-1 is much more effective in upregulating the synthesis of aggrecan than of small nonaggregating PGs in articular cartilage (Huch, K., et al., *Arthritis Rheum.* 40:2157–2161 (1997)), it is most likely that the enrichment in PGs reported here reflects principally the incorporation into the repairing matrix of newly-synthesized aggrecan molecules.

Second, the results indicate that OP-1 or related growth factors with similar modes of action are useful to stimulate matrix repair in vivo, not only after clinically-induced chemonucleolysis but also in the therapeutic treatment of disk degeneration.

Third, the data show that the combination of a proteoglycan-degrading enzyme and a growth factor provides a method of chemonucleolysis that is superior to the use of a proteoglycan-degrading enzyme such as chondroitinase ABC alone.

EXAMPLE 3

Osteogenic Protein-1 Stimulation of Cartilage Matrix Repair by Nucleus Pulposus and Annulus Fibrosus This Example demonstrates the efficacy of osteogenic protein in stimulating cartilage matrix repair by cells, specifically nucleus pulposus ("NP") and annulus fibrosus ("AF") cells, isolated from intervertebral discs ("IVDs").

In this Example, lumbar discs were isolated from New Zealand white rabbit and NP tissue was separated from AF tissue by dissection. NP and AF cells were separately isolated from the two tissues by sequential enzyme digestion and resuspended in 1.2% low viscosity sterile alginate, which was then formed into beads. The cells were separately cultured in DMEM/F-12 medium containing 10% FBS, with the medium being changed daily. After 7 days, each culture was subdivided into three groups. The first group was a control group that was not treated with OP-1. The second and third groups were grown in the presence of OP-1 for 72 hours, the second group being treated with 100 ng/ml of OP-1, and the third group being treated with 200 ng/ml of OP-1. Radiolabelled $^3$H-proline was added to the cultures for the last 4 hours of incubation with OP-1. After the incubation, collagen was extracted from the cultures, and the rate of collagen production was determined by measuring the radiolabel's incorporation into the extracts. Collagen production is associated with growth and repair of cartilage matrix. To determine the rate of cell proliferation, the content of each group's DNA was measured using Hoechst 33258 dye.

Osteogenic protein increased collagen production in both NP and AF cell cultures in a concentration-dependent manner. The third group incorporated more radiolabel than the second group, which in turn incorporated more radiolabel than the first control group. Osteogenic protein had a significant mitogenic effect at high concentrations, which accounts for some of the elevation in collagen production. Nonetheless, the rate of collagen synthesis was significantly increased even when increased cell proliferation is accounted for. These results suggest that osteogenic protein stimulates the growth and repair of extracellular matrix.

EXAMPLE 4

Development of Animal Models for Intervertebral Disc degeneration. Assessment of Morphologic, Biomechanical and Biochemical Changes in the Disc Due to Degeneration From among numerous animal models for disc degeneration, two rabbit models are selected, the stab-wounding of the annulus fibrosus model (Lipson, S. J. and Muir H, *Spine* 6:194–210 (1981) as well as the C-ABC intradiscal injection model (Kato, F. et al., *Clin. Orthop.* 253:301–308 (1990). These models are reproducible and biochemical changes have been described at different stages of degeneration.

White New Zealand rabbits, each weighing about 2.5 kg are used. Anesthesia is done with intramuscular ketamine 45 mg/kg and maintained with IV 5–10 mg/kg as needed and by oxygen/nitrous oxide by mask. Following prepping and draping, the posterolateral retroperitoneal approach is used to expose the anterior and lateral aspects of the discs. For the stab-wounding group, a transverse incision is made into the ventral annulus fibrosus using a number 11 blade. For the chemonucleolysis group, 0.25 cc of C-ABC (187 U/ml) is injected into the disc with a 28 gauge needle attached to a microsyringe. Each animal has two discs treated by stab-wound or chemonucleolysis and two control discs. The levels are randomly chosen. The wound is closed in layers and normal recovery is monitored 1 day after surgery. Three animals are sacrificed from both the stab-wound and chemonucleolysis groups at 2, 4, B, 12 and 24 weeks (a total of 30 rabbits).

Morphologic Assessment

MRI is obtained one day prior to sacrifice to determine the grade of disc degeneration. Additionally, to assess histological changes in the AF and NP, routine histology is performed on one treated and one control disc from each time period. For histology, the motion segments are fixed in phosphate buffered formalin, decalcified, embedded in parafin, sectioned, and stained with H & E. The MRI and histology results are graded by Thompson's criteria.

For MRI, the motion segments prior to loading are imaged at room temperature in a 1.5 Tesla cryomagnet (Signa scanner, General Electric Medical Systems, Milwaukee, Wis.) with a 4 or 5 inch diameter solenoid coils (Medical Advances. Inc., Milwaukee). Conventional spin echo (SE) sequences are used. T2-weighted images are obtained of each motion segments in the sagittal plane with conventional spin echo sequence. T2-weighted axial and parasagittal images are obtained with TE 33 and 80 msec., TR 2000 msec., 2 NEX, 1.0 mm slice thickness, 8 sq.cm. display field of view and 512×256 matrix.

The MRI images are examined for signal changes of the NP and inner AF (normal, dark, intermediate) and the presence of annular tears. Additionally, any structural changes such as disc height, involution of the outer annulus, the presence of myxoid degeneration, separation of the NP from the end-plate, vacuum phenomenon, Schmorl's nodes, and herniation are noted. Degenerative changes are graded from I to V based on Vemon-Roberts (Table 1). With the radial tear in mind, the discs are classified as I: normal, II: transverse tears or circumferential tears, III: radial tears, IV: advanced degeneration with loss of disc height. The sagittal images of the histologic sections are analyzed and graded from Thompson I to V (Table 2). The MRI and histology sections are correlated.

TABLE 1

MRI Grading (Vemon-Roberts)

| Disc Grade | Nucleus Pulposus | Annulus Fibrosus | End-Plate | Vertebral Body |
|---|---|---|---|---|
| I | Homogeneous bright, distinct margin | Homogenous dark gray | Single dark line | Margins rounded |
| II | Horizontal dark bands toward the annulus | Areas of brighter spots | Increase in central concavity | Tapering of margins |
| III | Decreased signal intensity Gray tone with stippling | Indistinguishable from nucleus pulposus | Line less distinct | Small dark projections from margins |
| IV | Proportions of gray signal Bright and dark regions larger | Bright and reduced dark signals contiguous with nucleus pulposus | Focal defects | Osteophytes <2 mm |
| V | Gross loss of disc Height Dark signals dominant | Signals contiguous with nucleus pulposus | Defects and areas of thickening | Osteophytes >2 mm |

TABLE 2

Description of the Morphologic Grades by Thompson

| Disc Grade | Nucleus Pulposus | Annulus Fibrosus | End-Plate | Vertebral Body |
|---|---|---|---|---|
| I | Bulging gel lamella | Discrete fibrous and uniform thickness | Hyaline | Margins rounded |

TABLE 2-continued

Description of the Morphologic Grades by Thompson

| Disc Grade | Nucleus Pulposus | Annulus Fibrosus | End-Plate | Vertebral Body |
|---|---|---|---|---|
| II | White fibrous tissue peripherally | Mucinous material between lamellas | Thickness irregular | Margins pointed |
| III | Consolidated fibrous tissue | Extensive mucinous infiltration Indistinct margins | Focal defects | Early osteophytes at margins |
| IV | Horizontal clefts | Focal disruptions | Focal sclerosis and fibrocartilage to bone | Osteophytes <2 mm |
| V | Clefts extend through nucleus pulposus, and the annulus fibrosus | | Diffuse sclerosis | Osteophytes >2 mm |

Biomechanical Tests

The goal is to determine changes in the dynamic axial and torsional stiffness of the disc and in the hysteresis response due to the various stages of disc degeneration when compared to normal disc. Biomechanical tests are performed within 12 hours after euthanasia of all animals, to preserve the biochemical composition as much as possible.

Protocol: Immediately after euthanizing animals, the lumbar motion segments are obtained, and extraneous soft tissues and posterior elements are removed leaving the vertebral body-disc-vertebral body units intact. The superior and inferior part of the each unit is cut by a slow speed diamond bone saw such that the resulting superior and posterior surfaces are parallel to the mid-transverse plane of the disc. The prepared specimen is subjected to a constant axial compressive load of 50 N for 30 min. Axial displacement resulting from the constant load is measured to investigate if there is any creep behavior. Then, the cyclic loads (50+20 N) is applied at frequencies of 0.5 and 5 Hz. The maximum load of 20 N is selected not to cause a permanent deformation of the disc tissue, failure of the end-plate or subchondral bone, or delamination or tears in the annulus. Load-unload cycles are repeated 20 times to ensure saturation for successive cycles, and a time interval of 5 minutes is allowed between each loading condition to ensure intradiscal pressure recovery. Following the compression tests, the specimen is kept in load-free condition for 30 minutes and is subjected to torsional moments applied in a similar manner. The mean torsional moment and the amplitude is 1.5 Nm and 0.5 Nm, respectively, and the loading frequencies are 0.1 and 1.0 Hz. While loading, signals from the load cell, LVDT (RVDT in the case of torsional tests), and the pressure sensor are sampled at 10, 50, 100, or 500, Hz. Vertebral body-disc-vertebral body units obtained from the experimental animals undergo cyclic compression and torsion tests once. However, the biomechanical tests are repeated twice on the vertebral body-disc-vertebral body units obtained first with intact discs and the second with stab wound discs. Biomechanical tests of the vertebral body-disc-body units with stab wounds are performed to investigate the biomechanical responses immediately after injury.

Load-displacement curves are obtained and analyzed to determine the dynamic stiffness and hysteresis. The dynamic stiffness is determined as the ratio of the input peak-to-peak load to the peak-to-peak displacement at the 20th cycle whereas the hysteresis is defined by the ratio of the area of the envelope of the loading and unloading paths to the area under the loading path. Load-intradiscal pressure curves are also obtained and analyzed to investigate the relationship between the applied load and intradiscal pressure responses. The intradiscal pressure slope dp/dl (KPa/N) is determined by dividing the peak-to-peak pressure by the peak-to-peak load, and the phase shifts (time lag between controlled load and intradiscal pressure) are represented as the area defined by the envelope of the loading and unloading paths. Creep behavior is described by the amount of axial and torsional displacement measured from the displacement-time curve obtained under constant static loading conditions, and the intradiscal pressure changes during the same time period is also determined from the corresponding intradiscal pressure-time curve.

Biochemical Studies

The purpose of these studies is to identify over time, changes in biochemical composition resulting from the stab-wounding or the C-ABC intradiscal injection rabbit disc degeneration models and to correlate the biomechanical characteristics with the biochemical composition of the disc. Following the biomechanical tests, from each vertebral body-disc-vertebral body unit, the disc is excised and biochemical tests that are described above are also performed. The entire lumber spinal segment is removed. Half of the specimens are analyzed for biochemical tests. The biochemical composition of the discs is quantified in terms of the proteoglycan, collagen (hydroxyproline) and collagen stable crosslink contents. The other half is fixed in 4% paraformaldehyde in PBS, decalcified. embedded in paraffin, sectioned and assessed by histology and immunostaining. Sagittal sections (5–8 μm) of each disc are stained with hematoxylin and eosin, as well as Safranin-O. Serial sections from each animal are tested for type II collagen and type I collagen immunoreactivity. Mouse monoclonal antibodies against human type II collagen and type I collagen are used as the primary antibodies. Sections are counterstained with Meier's hematoxylin prior to mounting.

EXAMPLE 5

Determination of OP-1 Mediated In Vivo Repair of Intervertebral Discs in Animal Models for Intervertebral Disc Degeneration This Example tests the potential usefulness of OP-1 injected intradiscally at the same time as the C-ABC solution or at the time of AF puncture, in promoting repair of the NP and AF.

Protocol: Twelve New Zealand rabbits weighing 3 kilograms are used for stab-wounding and stab-wounding+OP-1. Each rabbit has one disc that receives stab-wounding alone and another disc that receives stab-wounding+OP-1. An additional twenty-four rabbits are divided into 4 groups (control-saline injection, OP-1 alone, C-ABC alone, C-ABC+OP-1). Each rabbit has only two discs injected. After intravenous administration of sodium pentobarbital (25 mg/Kg), baseline radiographs are taken. Following inhalation of isoflurane, each rabbit is placed in a lateral prone position and the anterior surface of the lumbar disc is exposed through a posterolateral retroperitoneal approach. Chondroitinase-ABC (187 U/ml) alone, OP-1 (2 μg) alone or C-ABC premixed with OP-1 (2 μg) is injected into the two lower lumbar intervertebral discs (30 μl of solution per disc) with a 28 gauge needle attached to a microsyringe. For the control group, an equal volume of saline is injected. The wound is washed several times with sterile saline containing antibiotics and then closed with layered sutures. Three rabbits in each group are euthanized with an excess dose of pentobarbital at 2, 4, 8 and 16 weeks after injection. After euthanasia, radiographs are taken to evaluate disc space narrowing. The entire lumbar spinal segment is removed, fixed in 4% paraformaldehyde in PBS, decalcified, and embedded in paraffin. Sagittal sections (5–8 μm) of each disc are stained with hematoxylin and eosin, as well as Safranin-O. Serial sections from each animal are tested for type II collagen and, type I collagen immunoreactivity. Mouse monoclonal antibodies against human type II collagen and type I collagen are used as the primary antibodies, Sections are counterstained with Meier's hematoxylin prior to mounting.

From the foregoing, it will be observed that numerous modifications and variations can be effected without departing from the true spirit and scope of the present invention. It is to be understood that no limitation with respect to the specific examples presented is intended or should be inferred. The disclosure is intended to cover by the appended claims modifications as fall within the scope of the claims.

What is claimed is:

1. A method of chemonucleolysis, comprising:
   (a) administering a glycosidase that degrades chondroitin sulfate or hyaluronic acid to an intervertebral disk of a mammal, the intervertebral disk comprising a nucleus pulposus and an annulus fibrosus; and
   (b) administering an effective amount of a growth factor to the intervertebral disk within about 24 hours of (a), wherein the administration of the growth factor stimulates formation of a matrix component in the nucleus pulposus, annulus fibrosus or both the nucleus pulposus and the annulus fibrosus of the intervertebral disk.

2. The method of claim 1, wherein the glycosidase is a chondroitinase.

3. The method of claim 1, wherein the glycosidase is chondroitinase ABC.

4. The method of claim 1, wherein the glycosidase is chondroitinase AC, chondroitinase B, or chondroitinase C.

5. The method of claim 1, wherein the growth factor is an osteogenic protein.

6. The method of claim 5, wherein the osteogenic protein is OP-1.

7. The method of claim 1, wherein the growth factor is transforming growth factor β.

8. The method of claim 1, wherein the glycosidase and the growth factor are administered simultaneously.

9. The method of claim 1, wherein the glycosidase is chondroitinase AC, chondroitinase B, or chondroitinase C and the growth factor is OP-1 or transforming growth factor β.

10. The method of claim 1, wherein the administration of the growth factor stimulates proteoglycan formation in the nucleus pulposus.

11. The method of claim 1, wherein the administration of the growth factor stimulates collagen formation in the nucleus pulposus.

12. The method of claim 1 further comprising:
    (c) administering the glycosidase that degrades chondroitin sulfate or hyaluronic acid to the intervertebral disk of a mammal one or more times prior to (a).

13. The method of claim 1 further comprising:
    (c) repeating administration of the growth factor one or more times after the initial administration of the growth factor.

14. The method of claim 1 wherein the glycosidase is injected into the intervertebral disk.

15. The method of claim 1 wherein the growth factor is injected into the intervertebral disk.

16. A method of chemonucleolysis, comprising:
    (a) administering a glycosidase to an intervertebral disk of a mammal one or more times, the intervertebral disk comprising a nucleus pulposus and an annulus fibrosus; and
    (b) administering an effective amount of one or more growth factors one or more times to the intervertebral disk, wherein the initial administration of the one or more growth factors occurs within about 24 hours of the final administration of the one or more glycosidases and further wherein the administration of the one or more growth factor stimulates formation of a matrix component in the nucleus pulposus, the annulus fibrosus or both the nucleus pulposus and the annulus fibrosus of the intervertebral disk.

17. The method of claim 16, wherein the glycosidase is a chondroitinase.

18. The method of claim 16, wherein the glycosidase is chondroitinase AC, chondroitinase B, or chondroitinase C and the growth factor is OP-1 or transforming growth factor β.

19. The method of claim 16 wherein the glycosidase, growth factor or both are injected into the intervertebral disk.

20. The method of claim 16, wherein the glycosidase and the growth factor are administered simultaneously.

* * * * *